US012414839B2

(12) United States Patent
Davis

(10) Patent No.: US 12,414,839 B2
(45) Date of Patent: Sep. 16, 2025

(54) TONOMETER DISINFECTION SYSTEMS, METHODS, AND DEVICES

(71) Applicant: Andrew Peter Davis, Bellevue, WA (US)

(72) Inventor: Andrew Peter Davis, Bellevue, WA (US)

(*) Notice: Subject to any disclaimer, the term of this patent is extended or adjusted under 35 U.S.C. 154(b) by 420 days.

(21) Appl. No.: 17/955,195

(22) Filed: Sep. 28, 2022

(65) Prior Publication Data

US 2023/0100124 A1 Mar. 30, 2023

Related U.S. Application Data

(60) Provisional application No. 63/298,884, filed on Jan. 12, 2022, provisional application No. 63/249,570, filed on Sep. 28, 2021.

(51) Int. Cl.
*A61B 90/70* (2016.01)
*A61B 3/16* (2006.01)

(52) U.S. Cl.
CPC ............... *A61B 90/70* (2016.02); *A61B 3/16* (2013.01)

(58) Field of Classification Search
CPC .................................. A61B 90/70; A61B 3/16
USPC ........................................................ 600/398
See application file for complete search history.

(56) References Cited

U.S. PATENT DOCUMENTS

| | | | |
|---|---|---|---|
| 3,708,563 A | 1/1973 | Sells | |
| 4,824,641 A * | 4/1989 | Williams | B01L 3/0279 422/65 |
| 5,053,207 A | 10/1991 | Lervick | |
| 5,318,030 A | 6/1994 | Williams | |
| 7,708,938 B2 * | 5/2010 | Mariotti | A61L 2/28 134/22.12 |
| 2017/0304479 A1 | 10/2017 | Stein et al. | |
| 2019/0041307 A1 * | 2/2019 | Ingber | B01L 3/5085 |

OTHER PUBLICATIONS

International Search Report and Written Opinion of the International Searching Authority completed Dec. 19, 2022, in International Patent Application No. PCT/US2022/045118, 7 pages.

* cited by examiner

*Primary Examiner* — Alex M Valvis
*Assistant Examiner* — Chanel J Jhin
(74) *Attorney, Agent, or Firm* — Lowe Graham Jones PLLC

(57) ABSTRACT

Systems, methods, and devices for disinfecting tonometer probes are described. One example provides a specialized container that allows easy catching of a used probe without having to touch the probe, allows for the storage of multiple used probes, allows for simple disinfection of the probes without having to handle the probes or remove them from the container, allows for rinsing of the probes and container without handling the probes, and then allows for the simple insertion of the disinfected probes directly from the container without having to touch the probes or reinsert them into their specialized tubes.

24 Claims, 24 Drawing Sheets

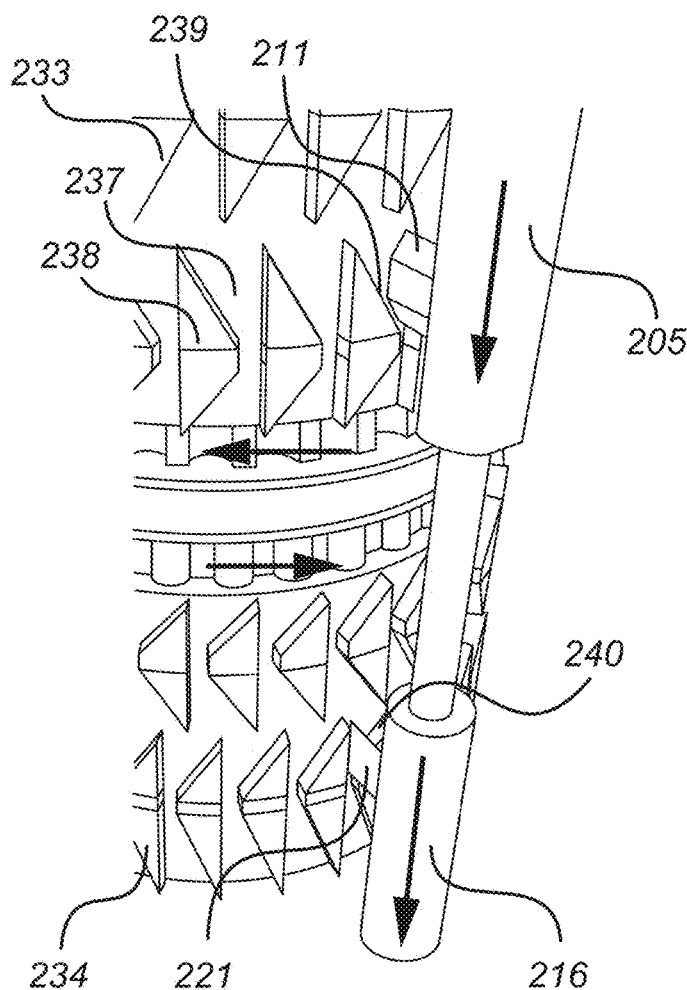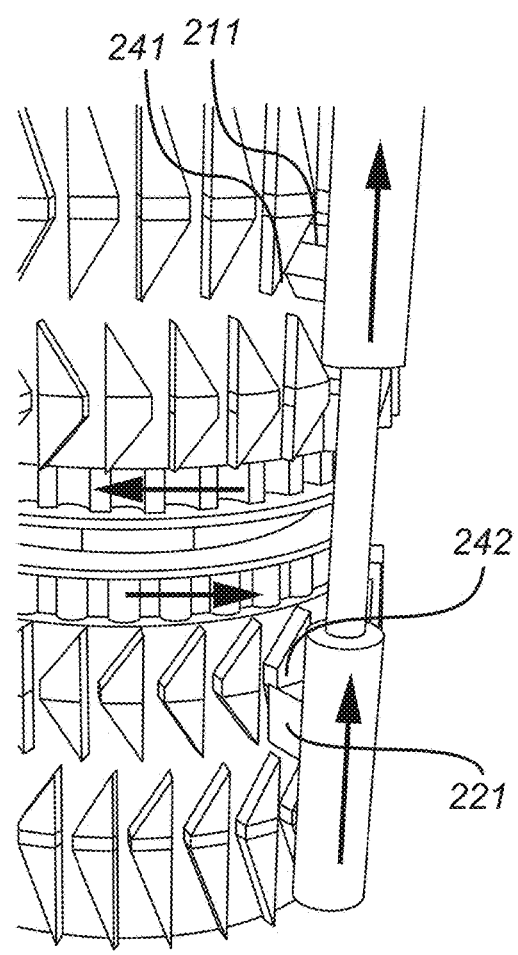
FIG. 15A
FIG. 15B

TONOMETER DISINFECTION SYSTEMS, METHODS, AND DEVICES

CROSS-REFERENCE TO RELATED APPLICATIONS

This application claims the benefit of priority from U.S. Provisional Patent Application No. 63/249,570, entitled "DISINFECTING SYSTEM FOR ICARE TONOMETER PROBES," filed Sep. 28, 2021; and U.S. Provisional Patent Application No. 63/298,884, entitled "COORDINATED SYSTEM AND METHOD FOR DISINFECTION OF REBOUND TONOMETER PROBES," filed Jan. 12, 2022, the contents of which are incorporated herein by reference in their entireties.

TECHNICAL FIELD

The present disclosure relates to devices, methods, techniques, and systems for disinfecting tonometer probes.

BACKGROUND OF THE INVENTION

A tonometer is a device for measuring the fluid pressure inside of an eye. A typical tonometer uses probes which are not meant to be handled directly. Consequently, it is quite burdensome to disinfect them one-by-one using gloves and then having to reinsert each one into its tube.

SUMMARY OF THE INVENTION

One embodiment provides a system for managing tonometer probes. The system includes a housing that includes an access port; and a plurality of tubes each configured to receive and hold a tonometer probe, wherein the access port is adapted to receive the tonometer probe from a tonometer and/or release the tonometer probe to the tonometer. In typical embodiments, the plurality of tubes is moveable within the housing such that each tube can be aligned with the access port, thereby facilitating passage of a probe from the tonometer into a tube or passage of a probe from a tube into the tonometer.

The system may further include a first cylindrical cartridge that holds the plurality of tubes circularly arranged about the central axis of the cartridge, wherein the first cartridge is configured to rotate about its central axis such that each of the tubes can be aligned with the access port to receive the probe from the tonometer or release the probe to the tonometer.

In some embodiments, the first cylindrical cartridge may be used for holding contaminated probes, wherein the access port is an input port for receiving contaminated probes from the tonometer. Such a system may further include a second cylindrical cartridge for holding clean probes; and an output port configured to release clean probes into the tonometer. The first and second cartridges may be removable from the housing. In some embodiments, the first and second cartridges may be held by the housing such that the central axis of the first cartridge is in alignment with the central axis of the second cartridge. In some embodiments, each of the tubes is open at a first end and closed at a second end, wherein each of the tubes includes at least one opening in its cylindrical wall, the opening located at the closed second end and configured to allow passage of fluid into the tube or out of the tube. In some embodiments, the first cylindrical cartridge includes: a base that contains the plurality of tubes; and a lid that is configured to rotate with respect to the base, wherein the lid includes a hole that is alignable with each of the plurality of tubes.

The housing of the system may include a first compartment configured to hold the first cartridge, wherein the tubes of the first cartridge each have an open end that points upward to receive tonometer probes; and a second compartment configured to hold the second cartridge, wherein the tubes of the second cartridge each have an open end that points downward to dispense clean tonometer probes. The first and second compartments may each be openable to receive a tonometer cartridge.

In some embodiments, the first compartment is above the second compartment and thus may be referred to as the "upper" and "lower" compartments, respectively. The housing of the system may include a lid that provides access to the upper compartment, such that the upper compartment can receive the first cartridge when the first lid is opened, wherein the central axis of the first cartridge is substantially vertical when the first cartridge is housed in the first compartment; and a hinge connected to the lower compartment that allows the lower compartment to be rotated between an open and closed position, such that the lower compartment can receive the second cartridge when in the open position, wherein the central axis of the second cartridge is substantially horizontal when the second cartridge is housed in the lower compartment in the open position, wherein the central axis of the second cartridge is substantially vertical when the second cartridge is housed in the lower compartment in the closed position. In some embodiments, the first or second compartment is moveable to facilitate loading or unloading of a cartridge.

The system may further include an actuator that causes the first and second cartridges to rotate in unison, such that the second cartridge advances to dispense a disinfected probe into the tonometer via the output port, and such that the first cartridge advances to align an empty tube with the input port. The actuator may be a rod, and wherein the rod includes a first tab that engages an outer surface of the first cartridge when the rod moves in a downward position thereby advancing the cartridge rotationally about its central axis. The rod may include a second tab that engages an outer surface of the second cartridge when the rod moves in an upward position, thereby advancing the second cartridge rotationally about its central axis, wherein the rod is biased upwards by a spring. The outer surface may include an angular protrusion. The actuator may be or include a stepper motor, lever, gears, or the like.

In some embodiments, the output port is a cup-like structure configured to mate with the tonometer to facilitate passage of a clean probe from the second cartridge into the tonometer. The system may also include an indicator that signals that the first cartridge is full or that the second cartridge is empty. The system may further include an indicator that displays how many disinfected probes remain in the system. The system may include an indicator that displays how many contaminated probes are held by the system. The system may also include a disinfection bath configured to hold one or more of the plurality of tubes, wherein the bath includes an indicator to notify a user that a period of time has passed. In some embodiments, the system includes an indictor that displays how many times the first or second compartment has been opened.

Some embodiments provide a process for managing tonometer tubes. The process includes loading a first cartridge into a housing, the first cartridge including a plurality of tubes that are configured to hold contaminated tonometer probes; loading a second cartridge into the housing (or a separate housing), the second cartridge including a plurality of tubes that are configured to hold disinfected tonometer probes; releasing, via an input port of the housing, a used tonometer probe into one of the plurality of tubes of the first cartridge; and releasing a disinfected tonometer probe from one of the plurality of tubes of the second cartridge; and receiving the disinfected tonometer probe into the tonometer. Releasing the disinfected probe may include first mating the tonometer with the housing via an outport port of the housing.

The process may further include advancing the first and second cartridges, thereby: exposing an empty one of the plurality of tubes of the first cartridge; and releasing the disinfected tonometer probe from the second cartridge into the tonometer. The process may further include removing the first cartridge from the housing; and placing the first cartridge in a disinfection bath.

BRIEF DESCRIPTION OF THE DRAWINGS

Preferred and alternative examples of the present invention are described in detail below with reference to the following drawings.

FIGS. 15A and 15B are schematic cutaway views of the second embodiment.

DETAILED DESCRIPTION OF THE PREFERRED EMBODIMENT

Embodiments described herein provide improved systems, methods, and devices for disinfecting tonometer probes that make it faster, easier, more intuitive, and with less chance of error. The described systems, devices, and methods could be used, for example, with iCare (TM) or other rebound tonometer probes.

Some embodiments provide a Coordinated System for Disinfection of Tonometer Probes ("the System"). The System may include a specialized container which allows easy catching of a used probe without having to touch the probe, allows for the storage of multiple used probes, allows for simple disinfection of the probes without having to handle the probes or remove them from the container, allows for rinsing of the probes and container without handling the probes, and then allows for the simple insertion of the disinfected probes directly from the container without having to touch the probes or reinsert them into their specialized tubes. Such a system would be very easy, efficient and cost saving.

Figure 1:
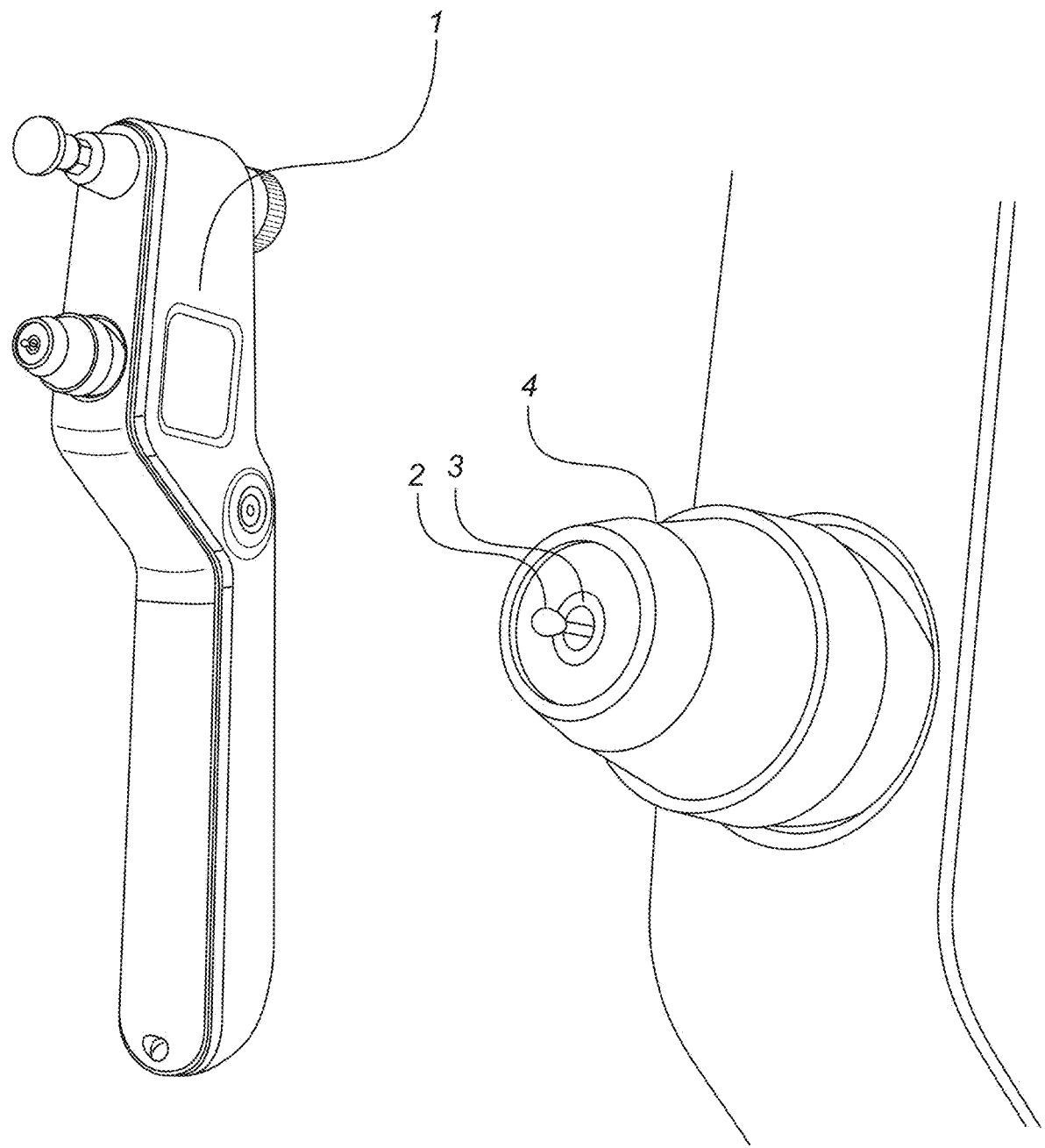
FIG. 1 shows an example of a prior art tonometer.

FIG. 1 shows an example of a commercially available tonometer 1, such as the iCare (TM) tonometer. Also shown is a probe 2 which needs to be inserted into a small hole 3 in a cone 4.

Figure 2:
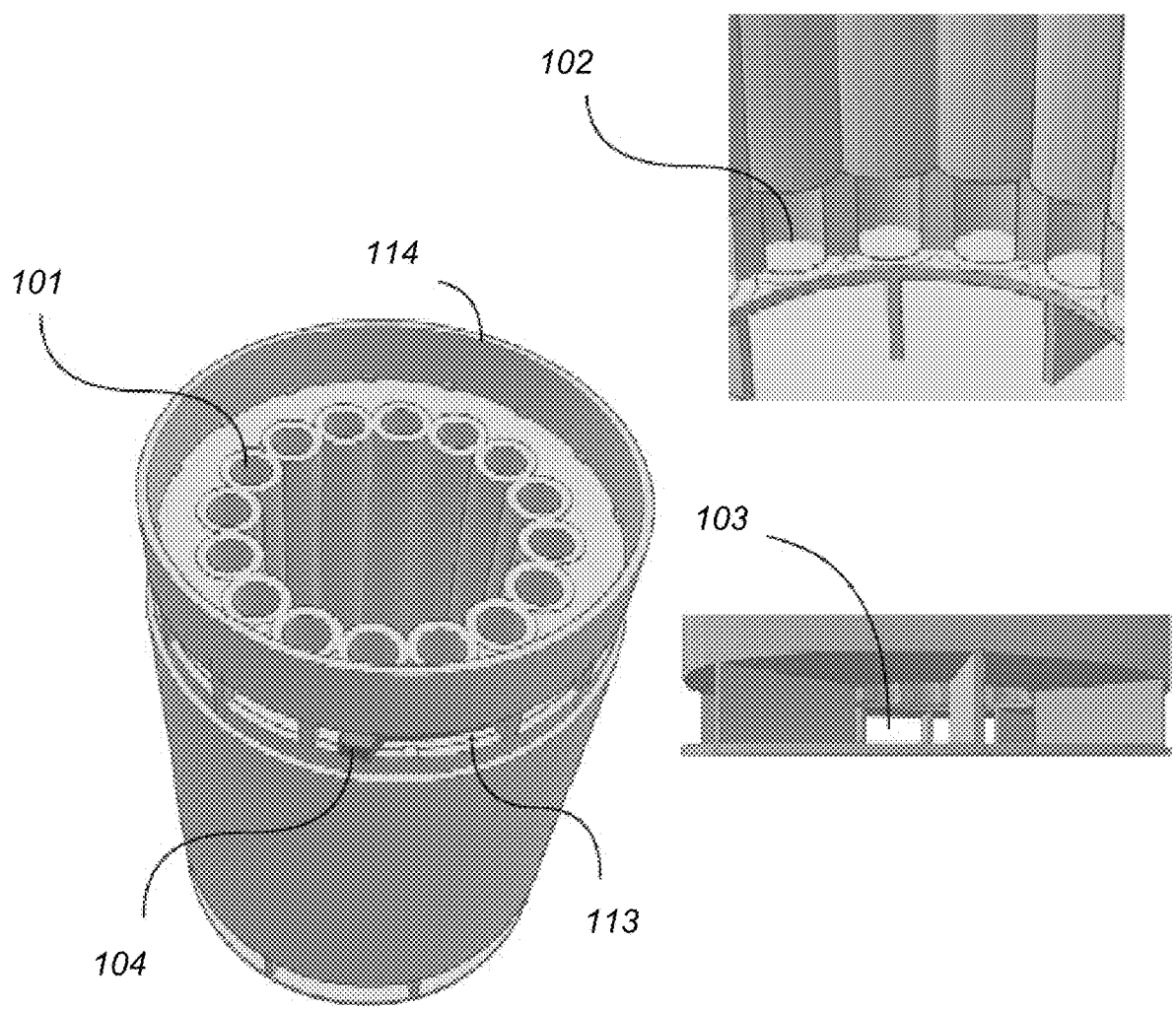
FIG. 2 shows views of the base of a probe container according to a first embodiment.

FIG. 2 shows views of a base of a probe container of a first embodiment of the System, which functions as a housing that contains multiple probe tubes 101 arranged peripherally in a circular arrangement. The bottom of each tube 101 is spaced a distance away from the bottom 102, to allow bubble-free filling of each tube with disinfecting or rinsing fluids. An opening at the bottom 103 allows entry of the fluids from the bottom up when immersing the container in the liquids. A flange 114 on the base allows for rotation of the top. Other embodiments may allow the liquids to be poured in from the top. A spring action protrusion 104 is located within a recess 113 on the side of the base.

Figure 3:
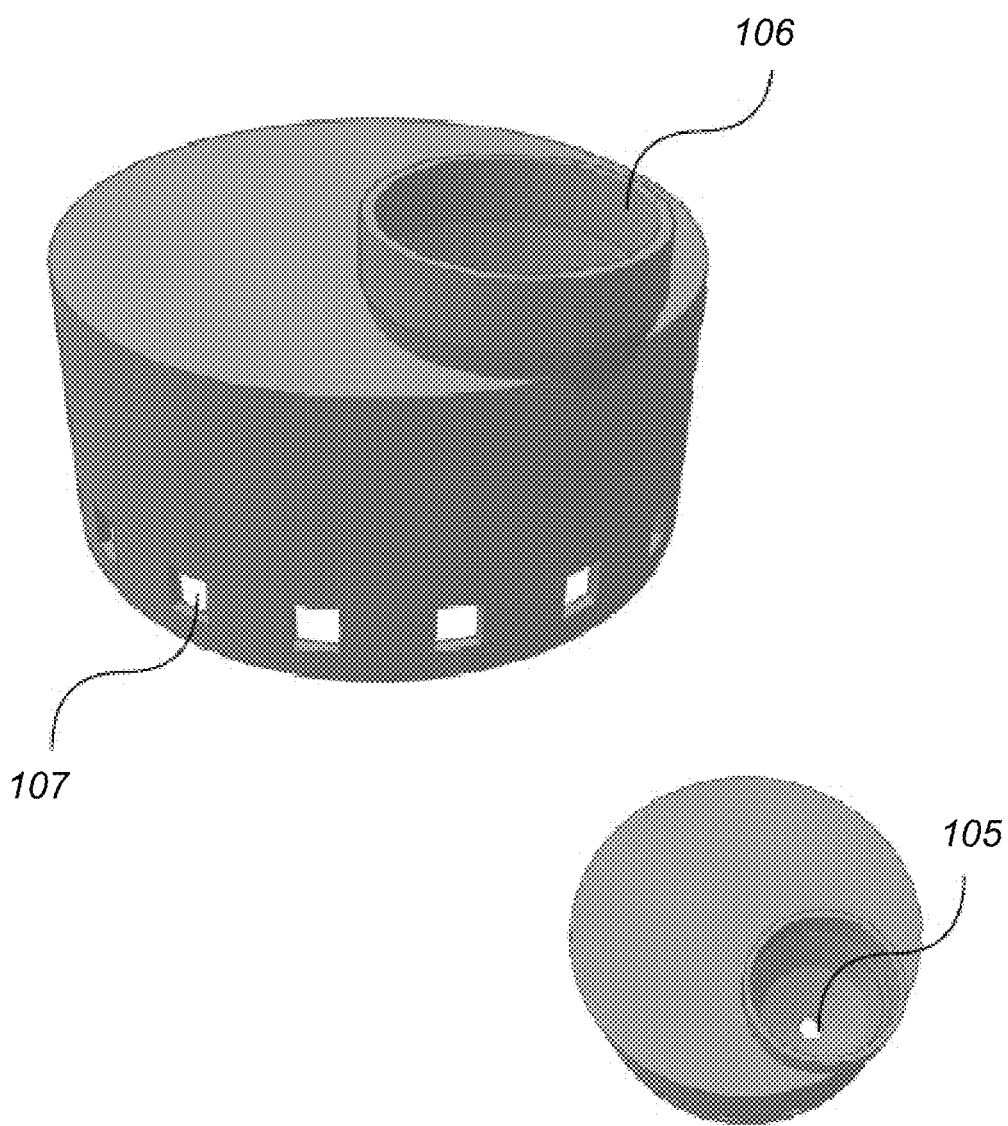
FIG. 3 shows the top of the probe container according to the first embodiment.

FIG. 3 shows the top of the probe container according to the first embodiment of the System. The container has an access port, which in this embodiment is an inverted cup-like member 106, with a small opening 108 at the bottom. A series of holes 107 on the side circumference is shown. The access port is used to receive or dispense tonometer probes as discussed further below.

Figure 4:
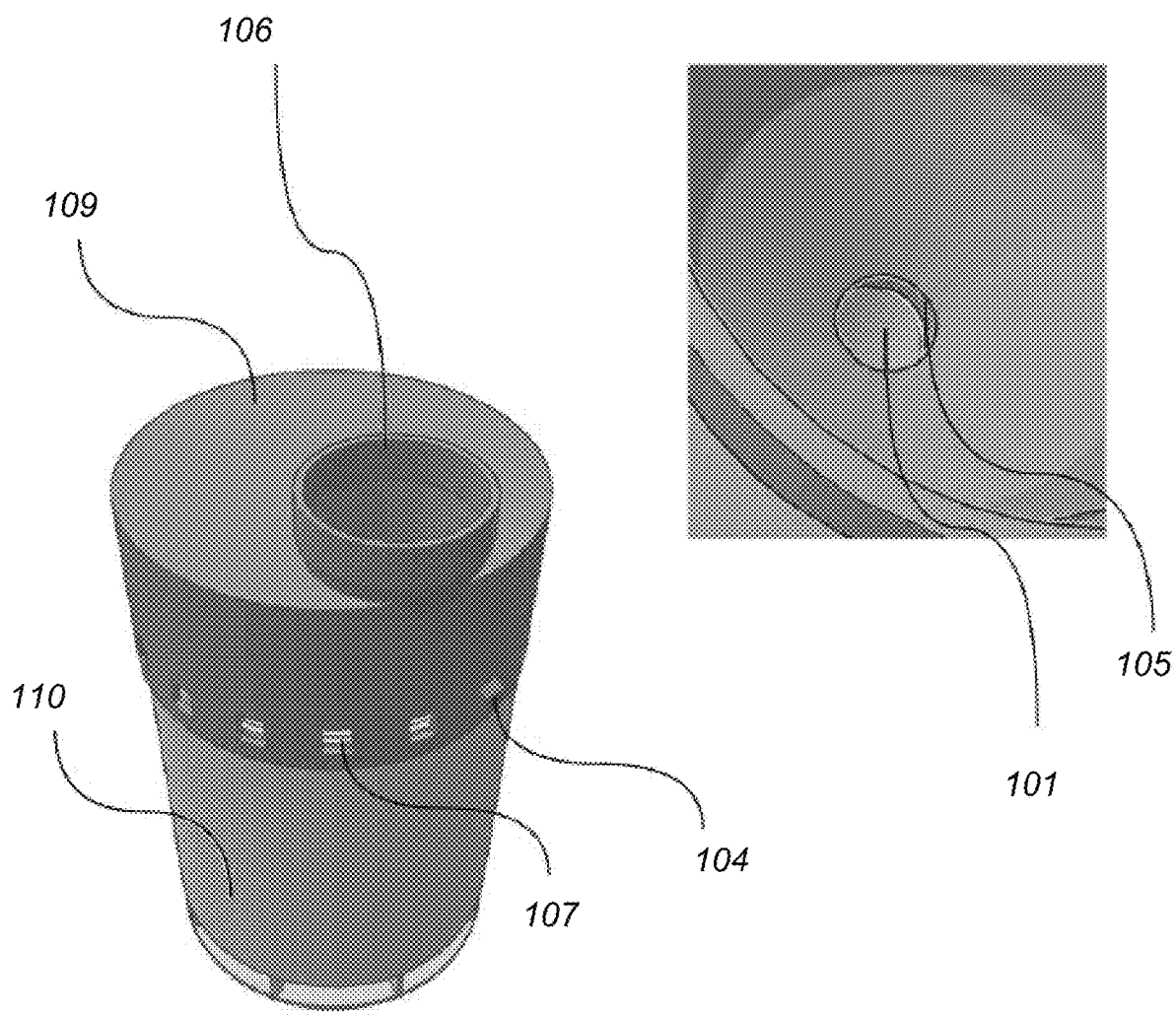
FIG. 4 shows the assembled container according to the first embodiment.

FIG. 4 shows the System assembled according to the first embodiment. The spring-action protrusion 104 on the base 110 aligns with the one of the circumferential holes 107 on the top 109, locking it into position, which ensures alignment of the hole in the bottom of the cup-like member 106 with the top opening 108 of the probe tubes 101.

Figure 5A:
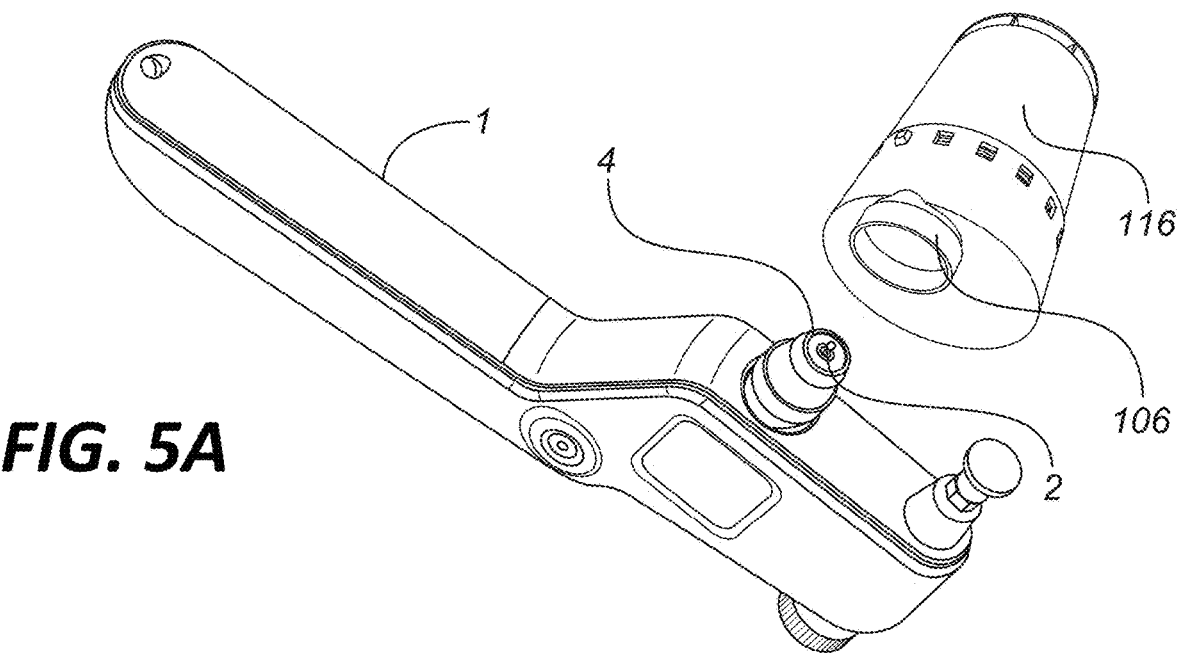
FIG. 5A illustrates the insertion of a clean probe from the container according to the first embodiment into a tonometer.

FIG. 5A shows the insertion of a clean probe into an example tonometer. The cone 4 of the inverted tonometer 1 is mated with the cup-like member 106 of the inverted System 116. This allows the probe 2 to fall out of the System 116 into the hole 3 in the center of the cone 4, without having to touch the probe. The user then rotates the top to advance to the next clean probe.

Figure 5B:
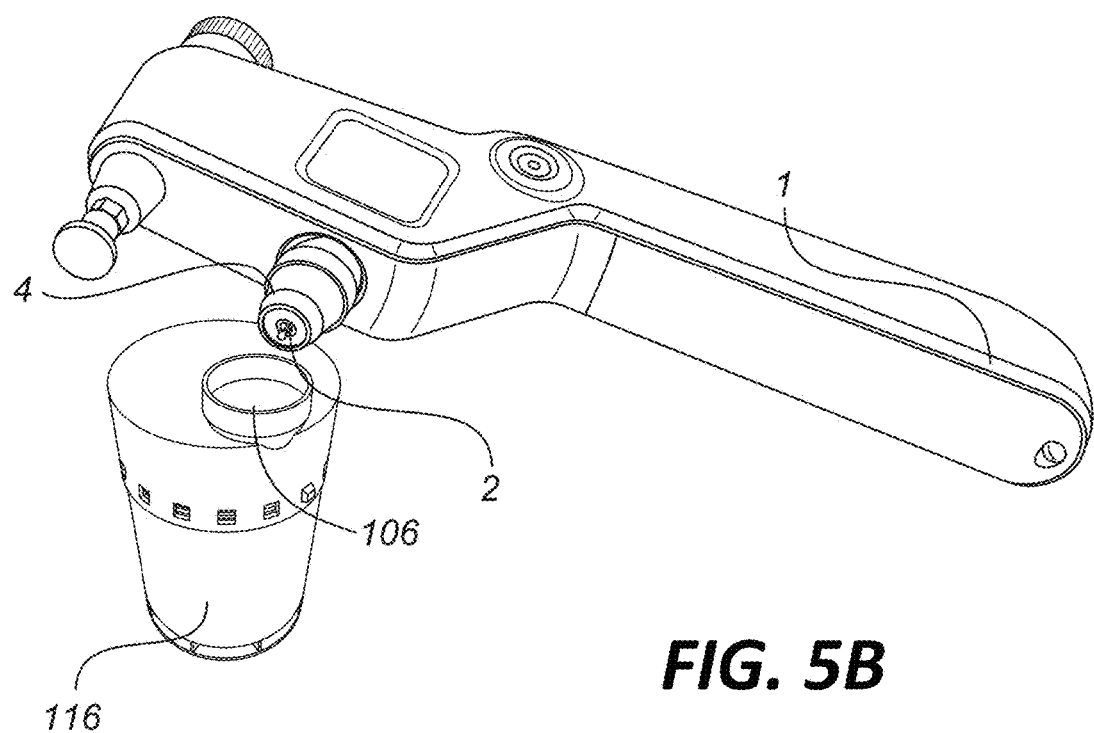
FIG. 5B illustrates the release of a contaminated probe from a tonometer directly into the container according to the first embodiment.

FIG. 5B shows the tonometer 1 releasing the contaminated probe 2 directly into the cup-like member 106 of the System 116. The cup-like member 106 mates with the cone 4 of the tonometer 1. This insures that the contaminated probe in the tonometer is perfectly aligned with the tube in the System, which then falls into the tube without the user having to touch the probe. The user removes the tonometer, and then rotates the top of the System to advance to the next tube.

In some embodiments, it is preferred that the user would have two System units. One would be used for contaminated probes and the other used for dispensing disinfected probes. Once all of the tubes of the dirty System are full, the user then immerses the System in the disinfecting solution to disinfect all of the probes at once. Then the System is immersed in rinsing solution and allowed to air dry, thus completing the cycle. The processed System is then deployed to dispense its supply of disinfected probes.

Other embodiments and variations may be configured to alert the user when the System and probes are dirty or clean. For example, the System may include a colored light that indicates whether the System holds dirty (e.g., red light) or clean (e.g., green light) probes. Other embodiments include a timing mechanism to signal the correct disinfection/rinse time. For example, the System may include a timer that rings or otherwise notifies (e.g., colored light, flashing light, text message notification, etc.) the user when the disinfection period has passed.

Figure 6A:
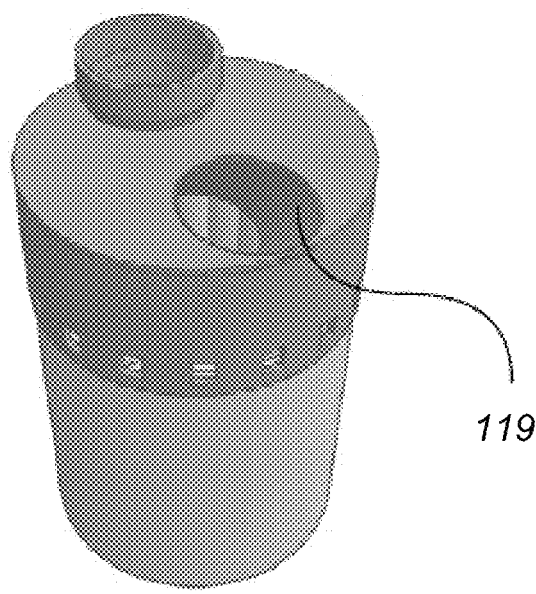
FIG. 6A shows an embodiment that includes a fill/pour spout.
Figure 6B:
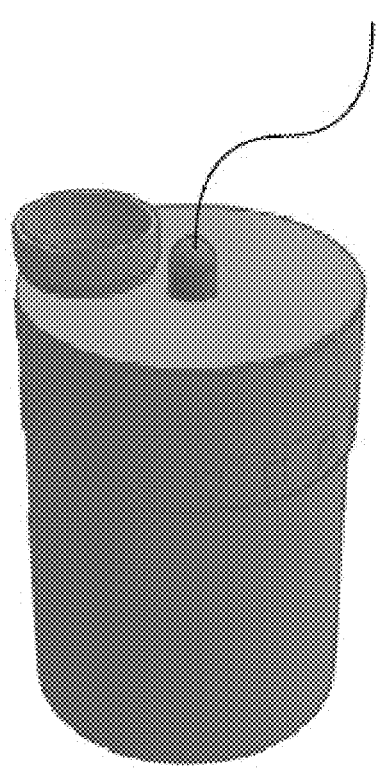
FIG. 6B shows an embodiment that includes a tube advance assembly.
Figure 7:
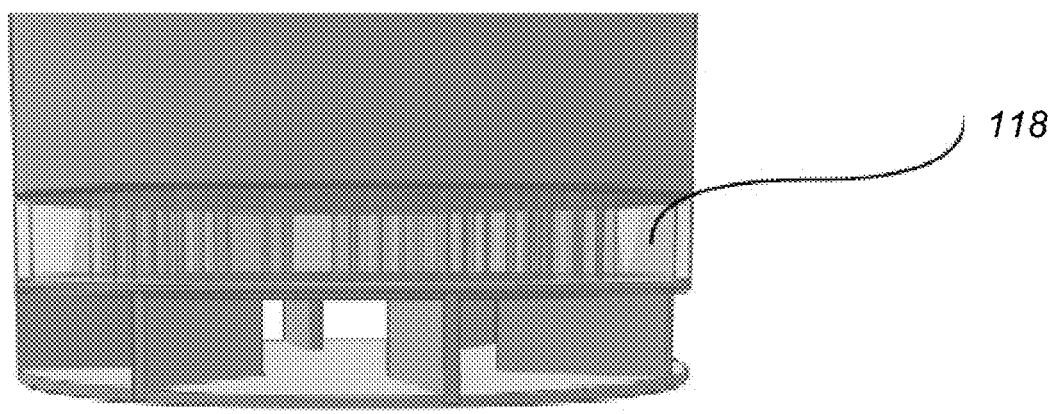
FIG. 7 shows an embodiment that includes a viewing window.

Variations for accessing and operating the System are also contemplated. For example, in some embodiments, the user can fill and empty the System from the top as shown in FIG. 6A with a fill/pour spout 119. In another embodiment, the user can advance the tube assembly with a push button type mechanism 120 similar to a ballpoint pen, as shown in FIG. 6B or electronic means. A further embodiment is configured to allow the user to visualize part of the tube to see which tubes contain a probe. For example, as shown in FIG. 7, the System container base includes a transparent plastic window 118 that shows the contents of the tubes.

Figure 8:
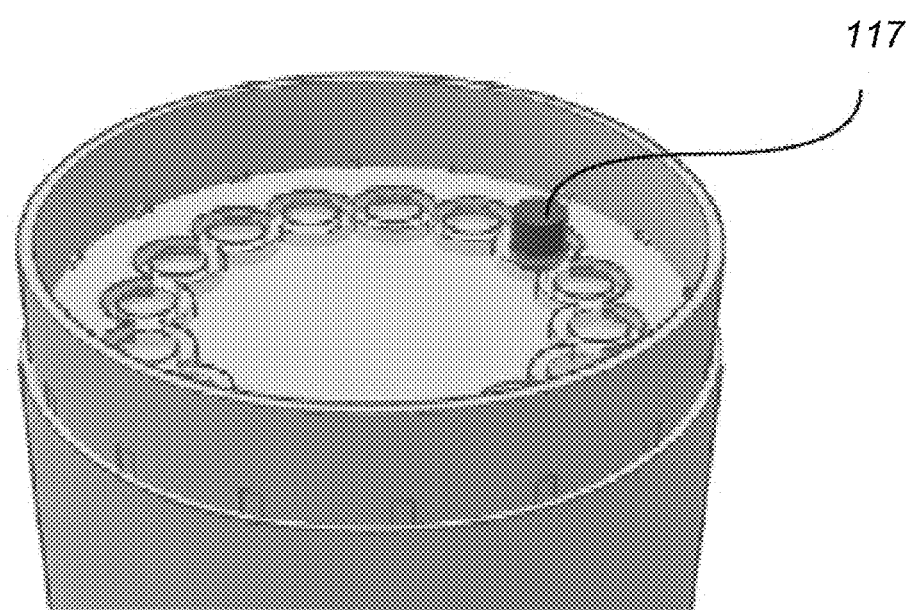
FIG. 8 shows a fullness indicator utilized in some embodiments.

FIG. 8 shows a fullness indicator utilized in some embodiments. In this embodiment, one of the tubes in the probe container is closed off at its top with a cap 117. This cap is typically colored red to serve as an indicator to the user that the container is full of used probes. Initially, when the container is empty, the cap is rotated so that it is in the first location adjacent to the access port in a counter-clockwise direction. As each used probe is added, the top is rotated clockwise with respect to the base. Eventually, when all tubes are full, the top will be rotated so that the red cap is visible through the access port, indicating to the user that the container is full and that it is time to disinfect the probes. In some embodiments, the container top includes a member (e.g., a tab) that catches against the cap 117 when it is rotated into position under the access port, thereby restricting any further rotation.

Figure 9:
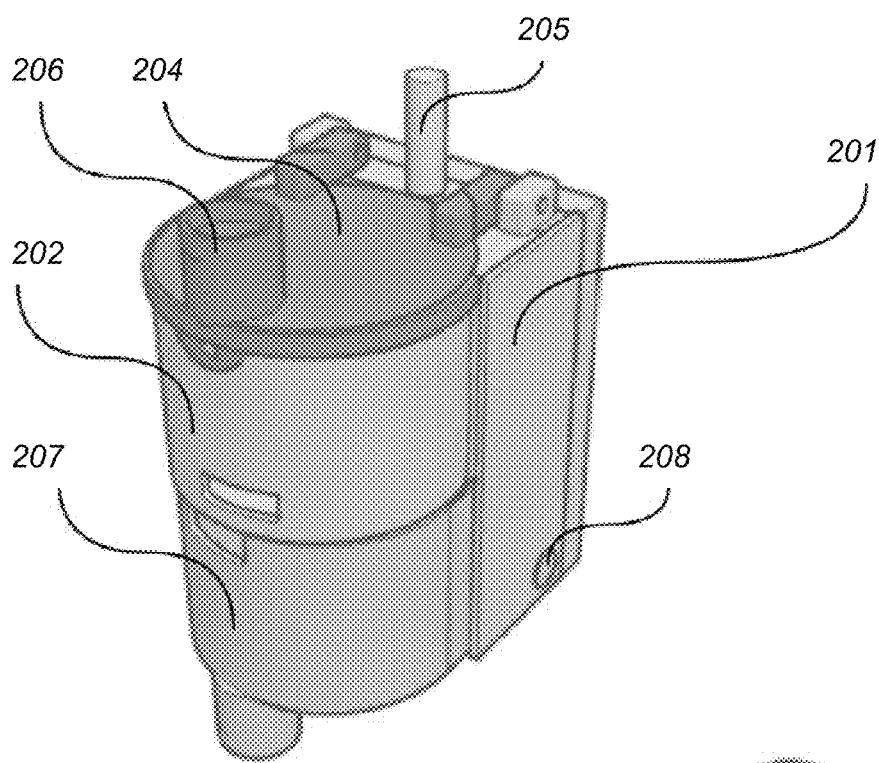
FIG. 9 shows a wall-mounted housing of a second embodiment.
Figure 9:
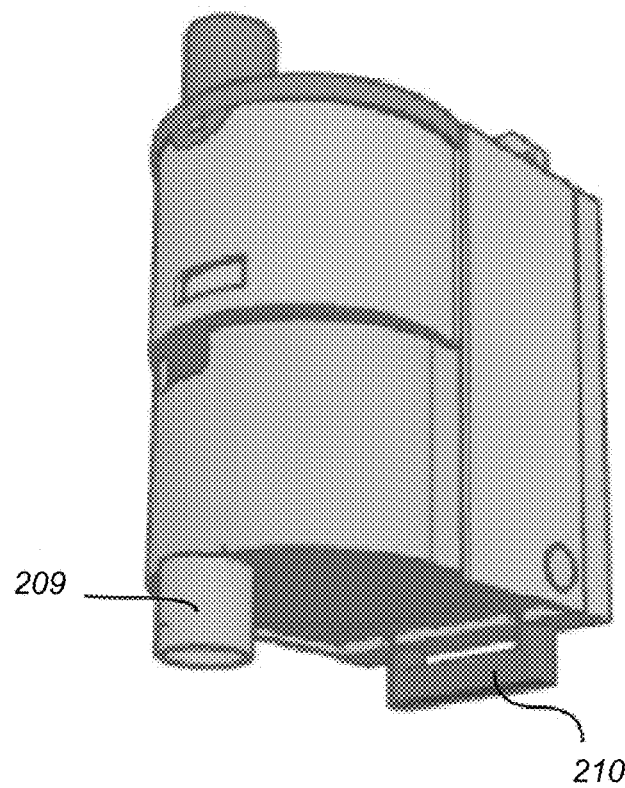

FIG. 9 shows a wall-mounted housing 201 of a second embodiment of the System. The upper compartment 202 of the housing 201 has a hinged lid 204. A vertical upper actuator rod 205 is located on the top of the housing behind the lid. An input port 206 is visible on the front of the lid. In this embodiment, the input port 206 is cup-shaped, although other embodiments may use other shapes, including cone, funnel, ramp, or the like. The rotating lower compartment 207 has a hinged attachment 208 at the base of the housing, and an output port 209 which in this embodiment is an inverted cup-like member on the underside of the rotating lower compartment 207 towards the front. A releasing bracket 210 is located on the underside of the housing towards the rear.

Figure 10:
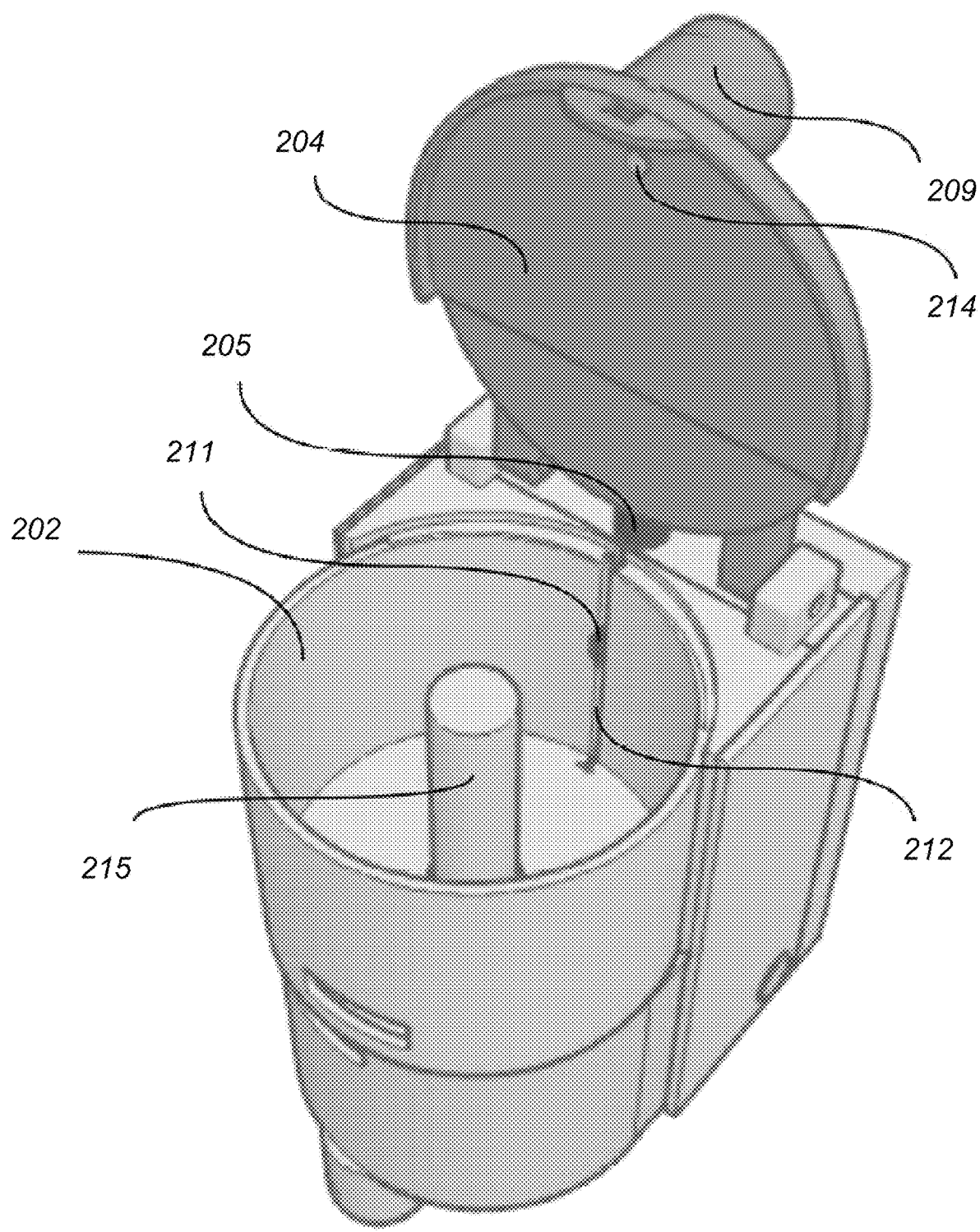
FIG. 10 shows the inside of an upper compartment of the second embodiment.

FIG. 10 shows the inside of the upper compartment 202, and the lower surface of the hinged lid 204. An upper actuator tab 211 protrudes from the upper actuator rod 205. The upper actuator rod 205 and upper actuator tab 211 can move vertically within the upper vertical grove 212 and shaft in the back of the upper compartment 202. A compression spring at the base of the shaft (not shown) allows the upper actuator rod 205 and tab 211 to move downward and then upward within the shaft when the top of the upper actuator rod is pressed down. A hole 214 at the bottom of the output port 209 of the hinged lid 204 is shown. There is a vertical post 215 rising from the bottom floor of the upper compartment. Note that in other embodiments, the lid over the upper compartment need not be attached via a hinge. In other examples, the lid can be attached via a post that allows the lid to be rotated to the side, latched on via spring clips, or the like.

Figure 11:
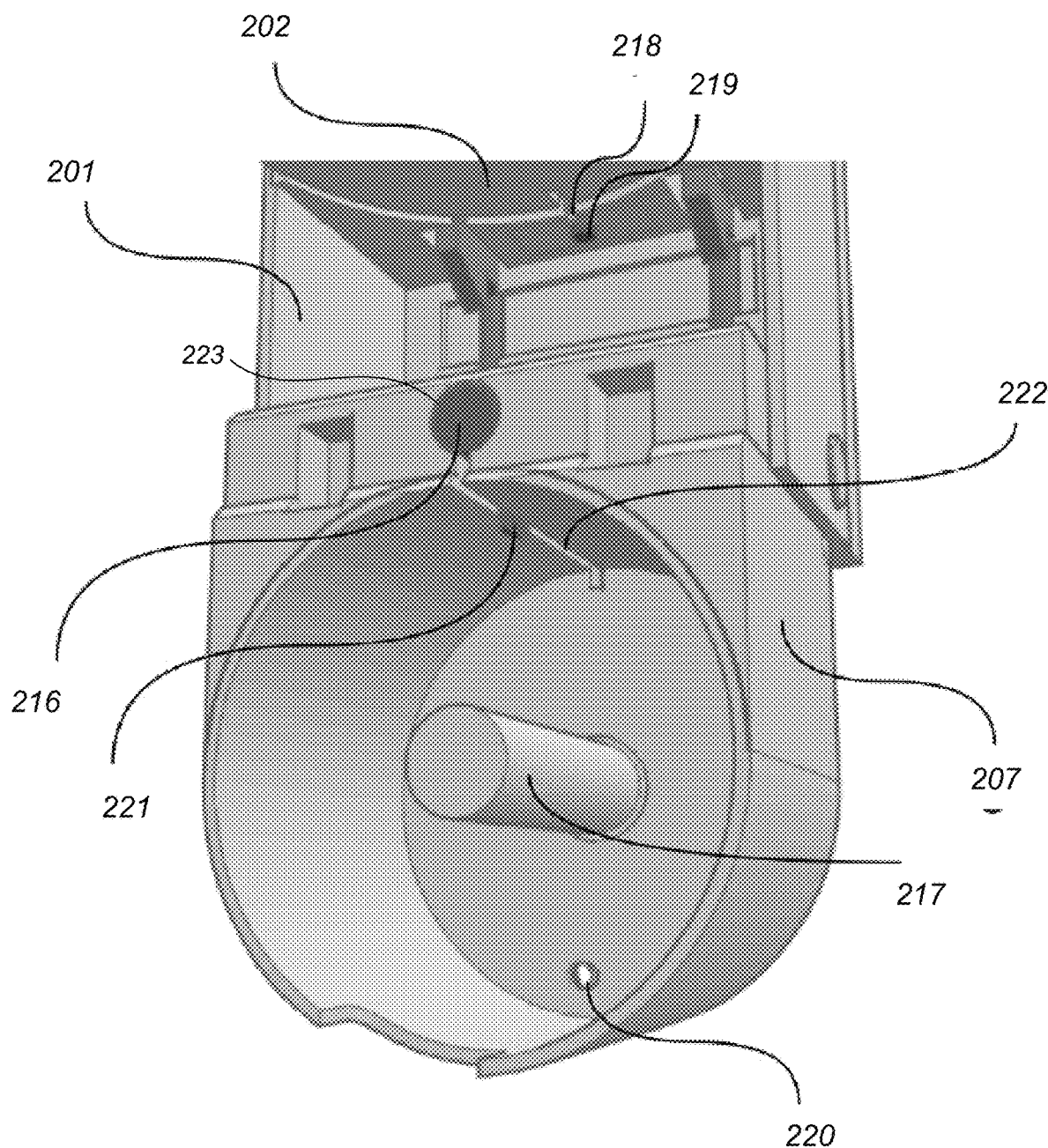
FIG. 11 shows the wall-mounted housing with its lower compartment in the open position.

FIG. 11 shows the wall-mounted housing 201 with the rotating lower compartment 207 in the open position, with its opening now facing forward. A central post 217 in the floor of the lower compartment is shown. The lower surface of the upper compartment 202 has opening 218 through which a narrow portion 219 of the upper actuator rod 205 can pass. A lower actuator rod 216 and lower actuator tab 221 can move up and down through the lower vertical groove and shaft 222 in the back of the rotating lower compartment 207. An opening 223 in the top of the rotating lower compartment 207 allows the narrow portion 219 of the upper actuator rod 205 to pass into the lower vertical groove and shaft 222 (when the rotating lower compartment 207 is in the closed position). The opening 223 is smaller in diameter than the lower actuator rod 216 in order to limit movement of the rod 216 out of the compartment 207, as the rod 216 is biased upwards by a spring. A small hole 220 is seen on the floor of the rotating lower compartment 220. This hole 220 aligns with the output port 209 to allow passage of tonometer probes out of the compartment/cartridge and into a tonometer.

Figure 12:
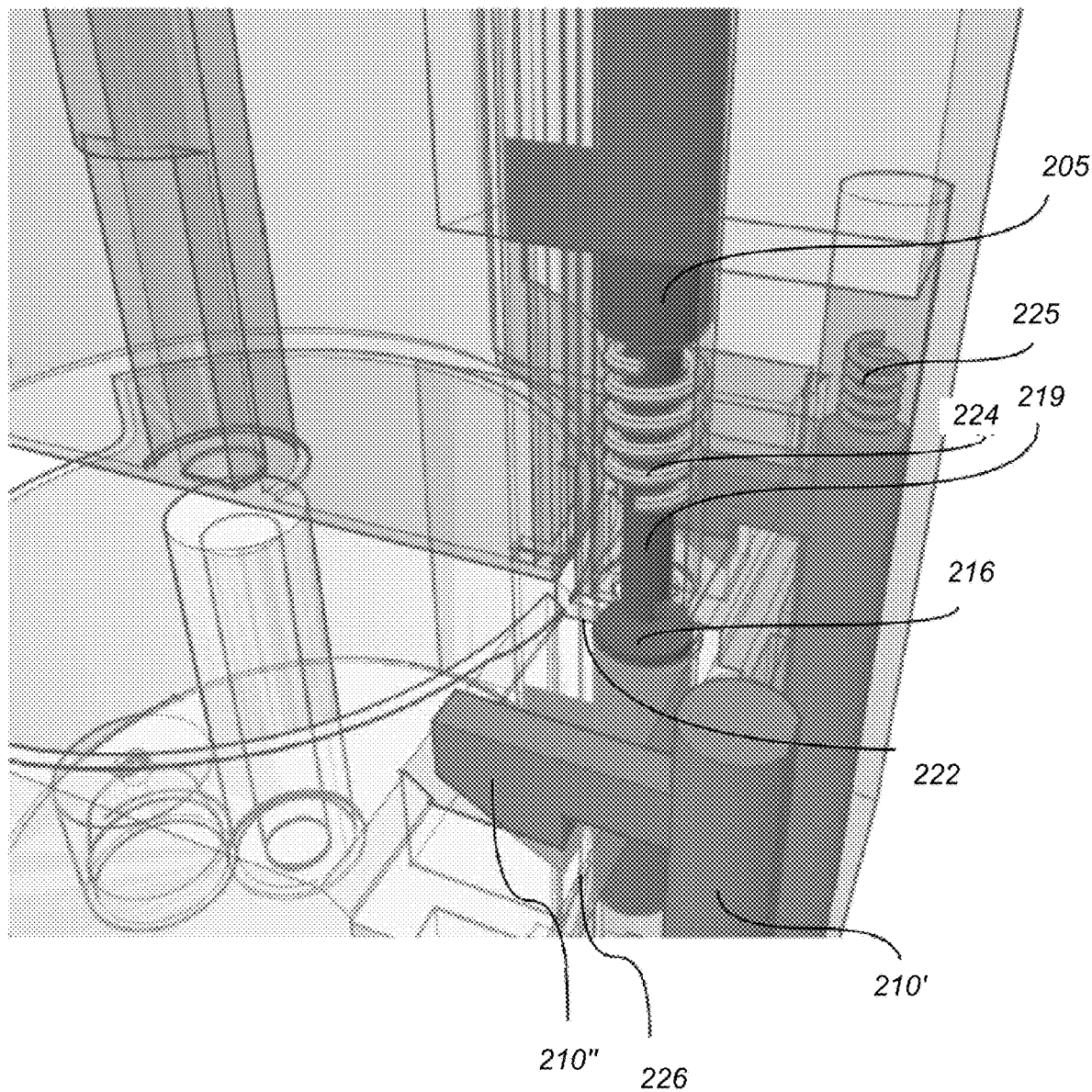
FIG. 12 is a transparent cutaway view of the second embodiment.

FIG. 12 is a transparent cut-away view of the second embodiment. The narrow portion 219 of the upper actuator rod 205 passes into the lower vertical groove and shaft 222 to contact the top of the lower actuator rod 216, allowing the upper and lower activator rods and tabs to move up and down in unison. Springs 224 are shown. The releasing bracket 210 has two arms 210' and two releasing hooks 210" and springs 225. Pressing the releasing bracket 210 disengages the releasing hooks 210" from the latching rims 226 of the housing.

Figure 13:
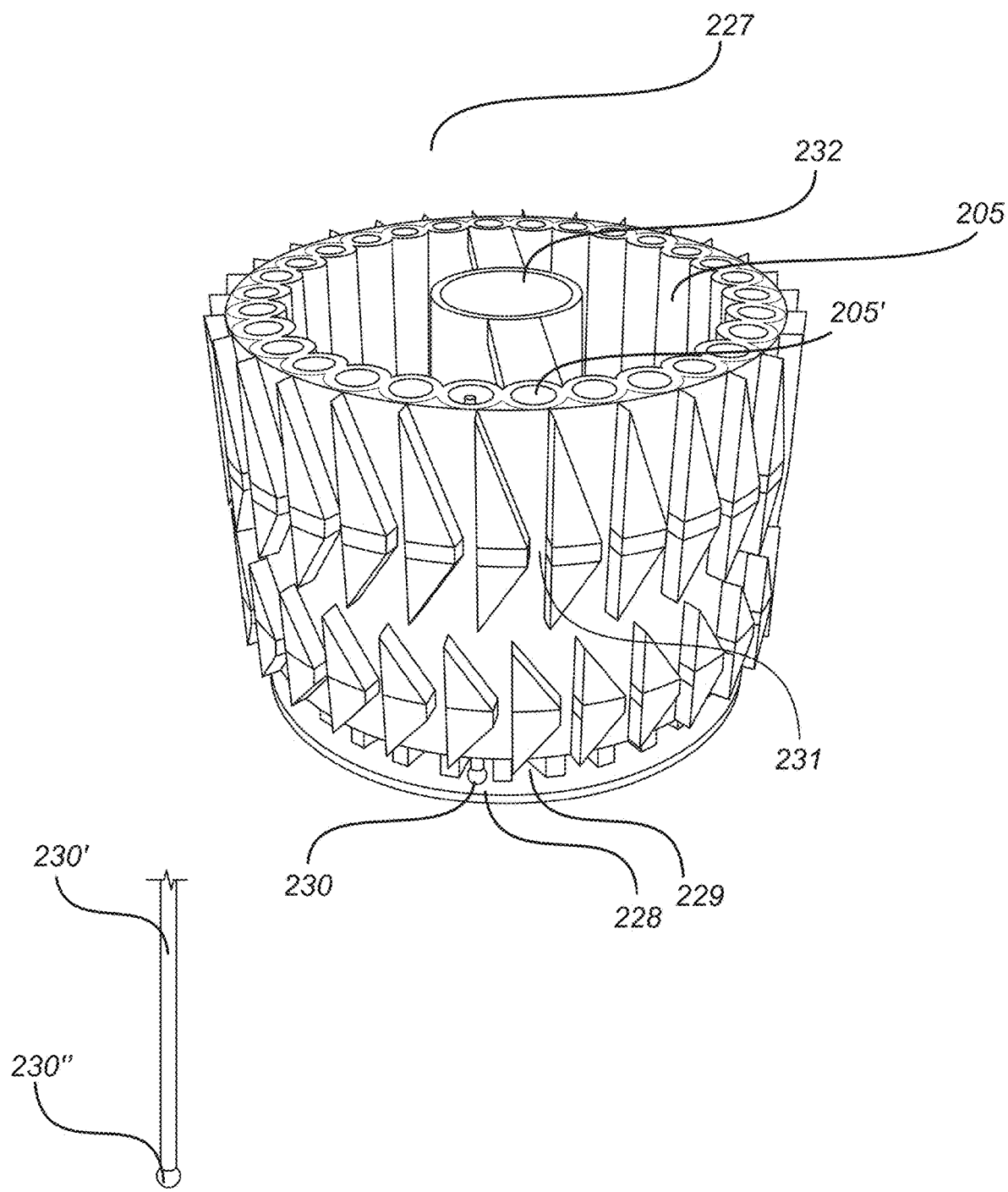
FIG. 13 shows a probe cartridge according to the second embodiment.

FIG. 13 shows a probe cartridge 227, containing multiple probe tubes 205 arranged peripherally in a circular arrangement. The tubes are each open at the top 205', and have a side opening 229 above the cartridge floor 228. The side openings 229 allow viewing of the probes 230 in the tubes, as well as allowing the disinfectant to fill from the bottom. There are positioning channels 231 on the outer surface of the cartridge aligned with each of the probe tubes. A central pillar 232 is shown. A probe is shown with its long metal shaft 230' and with a small plastic ball 230" at the bottom.

Figure 14:
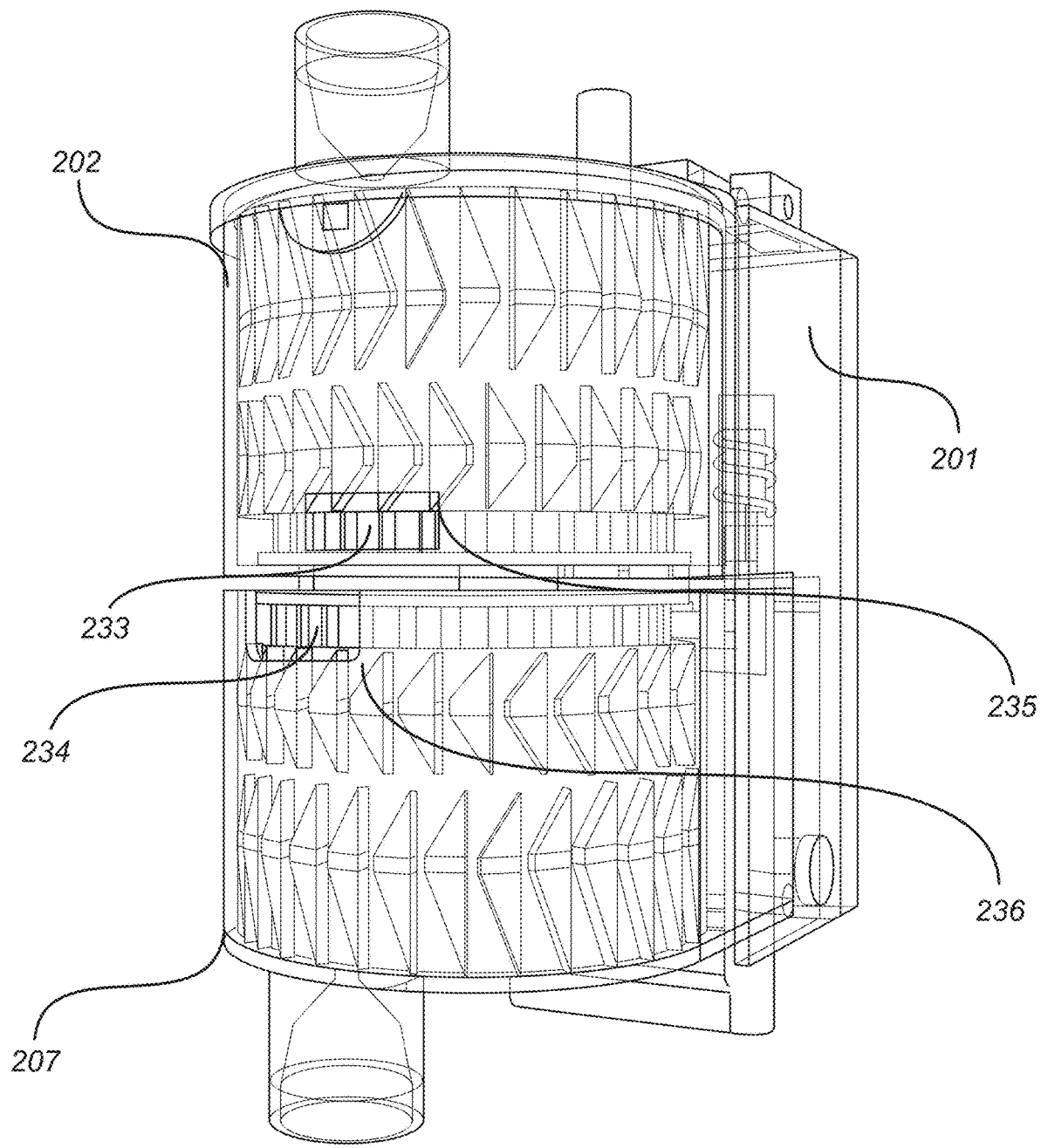
FIG. 14 shows the housing with the upper compartment containing the probe cartridge according to the second embodiment.

FIG. 14 shows the housing 201 with the upper compartment 202 containing an upper probe cartridge 233 visible thru an upper window 235 and lower rotating compartment 207 containing a lower probe cartridge 234 visible through a lower window 236. It should be noted that the lower probe cartridge 234 is in an inverted position with respect to the upper probe cartridge.

FIGS. 15A and 15B show schematic cut away views. In FIG. 15A, the positioning channels 237 are formed by spaces between circumferential triangular protrusions 238 on the outer surface of the upper probe cartridge 233 and inverted lower probe cartridge 234. The positioning channels are fashioned so that when the actuator rods 205 and 216 are pushed downwards, the actuator tabs 211 and 221 engage the first rotational surface 239 and 240, causing the upper probe cartridge 233 to begin a clockwise rotation and the lower inverted probe cartridge 234 to begin a counter-clockwise rotation. In FIG. 15B, the springs push the actuator rods 205 and 216 back up, the actuator tabs 211 and 221 engage the second rotational surface 241 and 242 causing the upper and lower probe cartridges 233 and 234 to finish their rotation to the next position.

Figure 16A:
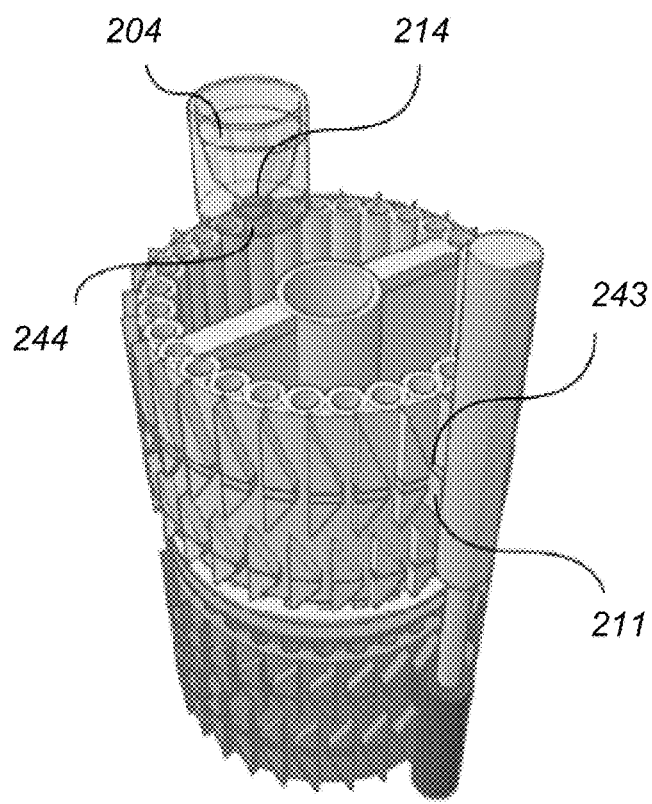
FIGS. 16A and 16B illustrate operation of the activator tab of the second embodiment.
Figure 16B:
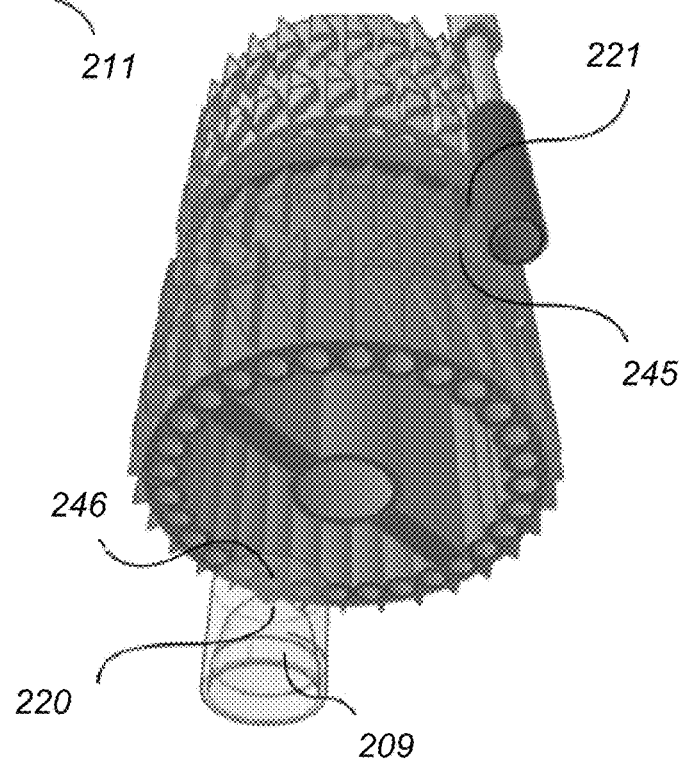

FIG. 16A shows that when the upper activator tab 211 is in the home position 243 at the narrowest portion of the positioning channel, the opening of one of the probe tubes 244 is exactly aligned with the hole 214 in the cup like member of the lid 204. FIG. 16B shows that when the lower activator tab 221 is in the home position 245 at the narrowest portion of the positioning channel, the opening of one of the inverted probe tubes 246 is exactly aligned with the hole 220 in the cup like member of the rotating lower compartment 209.

Figure 17A:
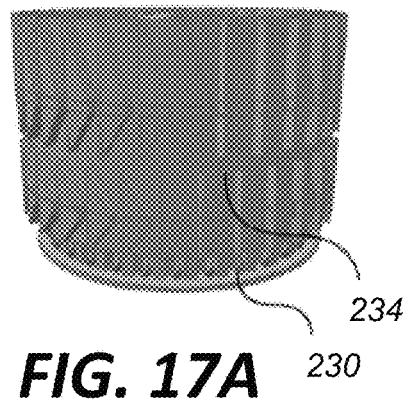
FIGS. 17A-17I show a method of utilizing the second embodiment.
Figure 17B:
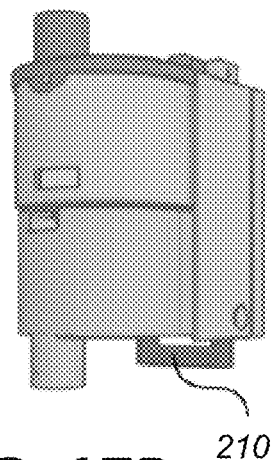
Figure 17C:
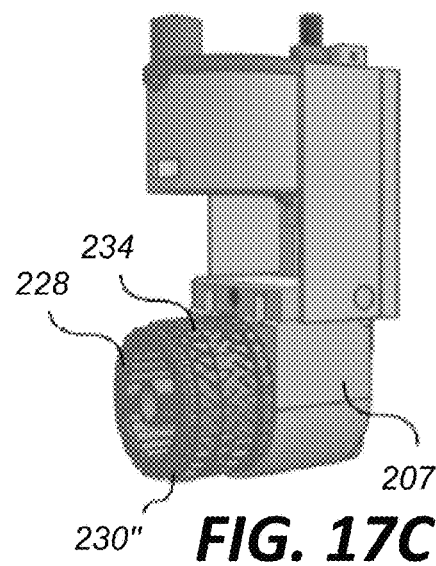
Figure 17D:
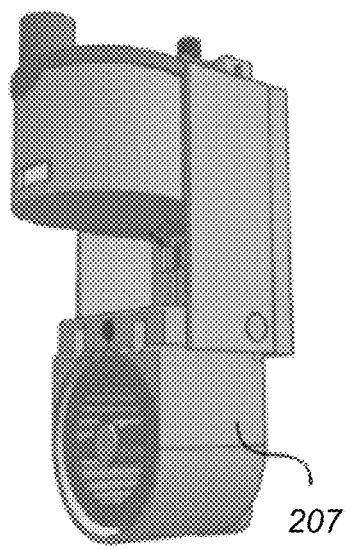

FIGS. 17A-17I show a method of utilizing the present invention according to the second embodiment. FIG. 17A shows a probe cartridge 234 filled with clean probes 230. In FIG. 17B, the releasing bracket 210 is pressed. This opens the rotating lower compartment 207, as shown in FIG. 17C. The clean probe filled cartridge 234 is next inserted horizontally into the open rotating lower compartment 207, with the top of the cartridge and the open end of the tubes inserted first, and with the floor 228 of the cartridge and the ball end 230" of each probe inserted last. After it is fully inserted, as shown in FIG. 17D, the rotating lower compartment 207 is rotated back into position.

The cartridge 234 here is shown being loaded horizontally into the housing. This is done because the cartridge 234 must be oriented "upside down" (tube opening facing downward) in operation so that clean probes can fall out of the cartridge and into the tonometer. The cartridge 234 is loaded horizontally so that the clean probes do not fall out during loading. Note that the cartridge 234 need not necessarily be exactly horizontal during loading, as slight displacement from the horizontal may be acceptable because the friction of a tonometer probe against the inner wall of a containing tube may still keep the probe from falling out at some angles (e.g., less than 10 degrees from horizontal).

Note that the cartridge 234 need not necessarily be loaded in an exactly horizontal position. More generally, the cartridge 234 can be loaded in a substantially horizontal position, which includes any angle from the horizontal at which the probes will not fall out by the force of gravity. Similarly, in operation the top and bottom cartridges are in a substantially vertical position alignment, which includes any angle at which the probes will fall into or out of a tube by the force of gravity.

Clean probes may be loaded in other ways in other embodiments. For example, another embodiment may have a housing with two compartments each having a lid, akin to the lid of the first upper compartment of the second embodiment. In such an embodiment, the entire housing may be configured to rotate on an axis that is orthogonal to the cartridge axis. Because there is no fixed upper and lower compartment, the compartments are instead referred to as "clean" and "used." In operation (when dispensing and receiving probes), the used compartment is the upper compartment, and the clean compartment is the lower compartment. To load the System, the housing is rotated 180 degrees so that the clean compartment is at the top. The lid is opened and the clean cartridge is inserted, with the tube openings facing upwards, eliminating any risk that clean probes will fall out of the tubes during loading. The lid is then closed and latched. Then the housing is rotated 180 degrees so that the tube openings of the clean cartridge are now facing downwards, ready to be gravity-fed into the tonometer as needed. In addition, when the used compartment is at top, the lid of the used compartment can be opened to replace the cartridge containing used probes with an empty cartridge.

Figure 17E:
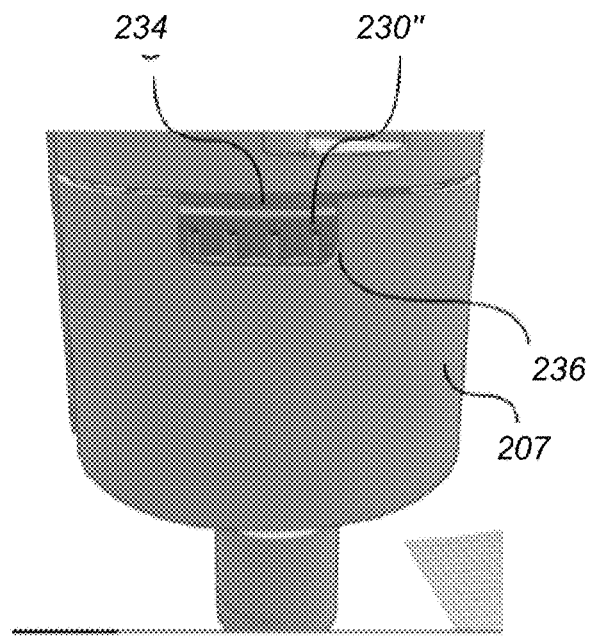

FIG. 17E shows the closed rotating lower compartment 207 with the lower cartridge 234 in an inverted position, and with the ball end 230" of the probes 230 visible through the lower window 236. Inserting the cartridge in a horizontal direction keeps the probes from falling out.

Figure 17F:
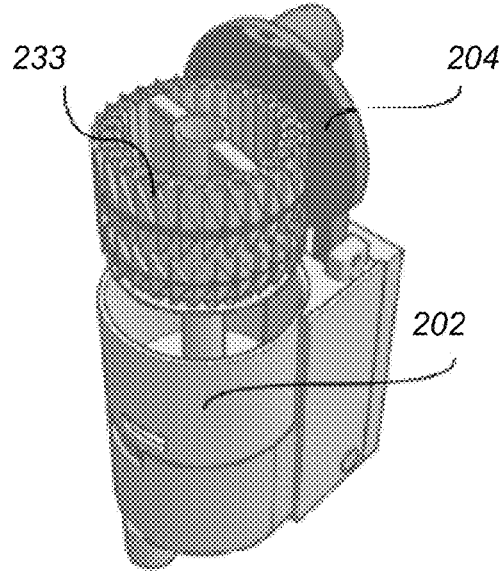
Figure 17G:
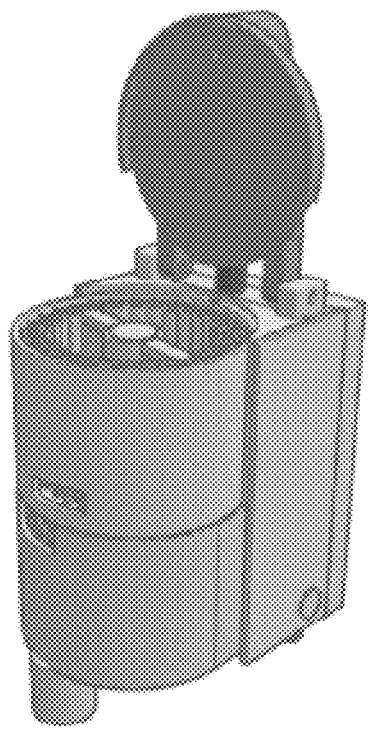
Figure 17H:
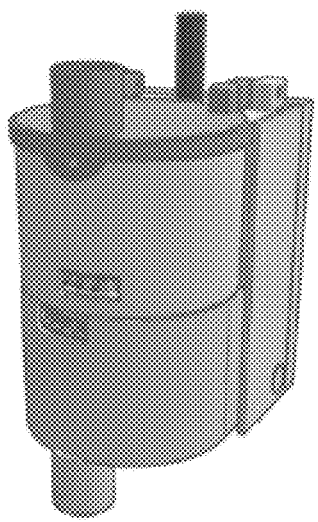
Figure 17I:
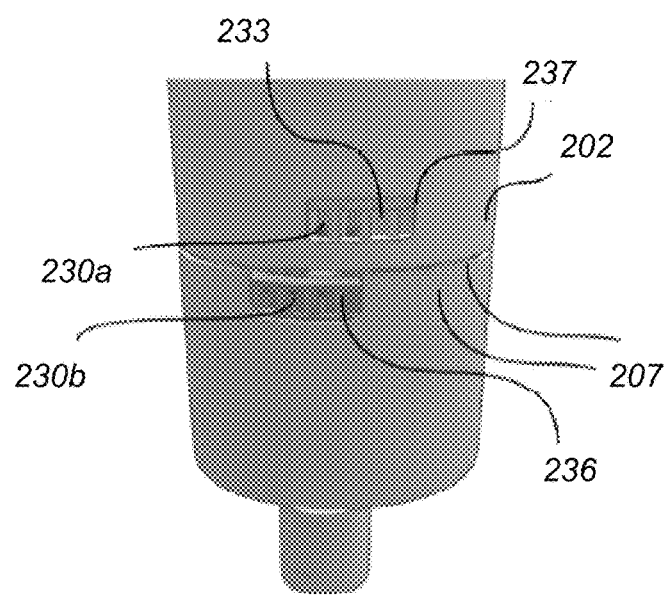

In FIGS. 17F-17H, the hinged lid 204 on the upper compartment 202 is opened and an empty cartridge 233 is inserted and the lid is closed. In FIG. 17I, the contaminated probes 230a in the upper cartridge 233 are visible in the upper window 235 of the upper compartment 202. The inverted clean probes 230b in the lower cartridge 234 are visible in the lower window 236 of the rotating lower compartment 207.

Figure 18:
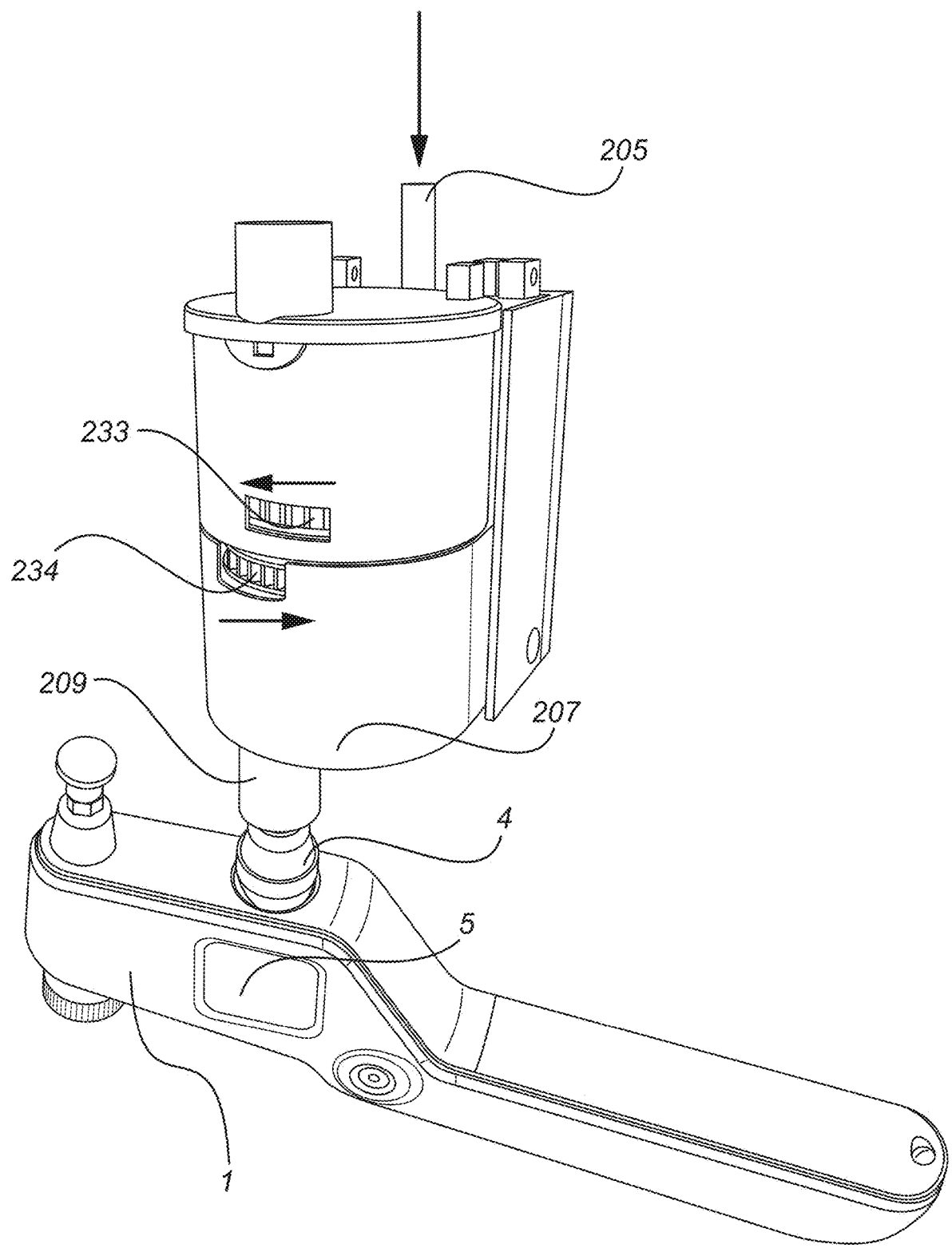
FIG. 18 shows how to insert a clean probe into a tonometer.

FIG. 18 shows how to insert a clean probe into the tonometer. The tonometer 1 is held under the System such that the cone 4 of the tonometer 1 is mated with the output port 209 on the rotating lower compartment 207. Once it is in position, the upper actuator rod 205 is pressed down and released, causing both upper cartridge 233 to rotate clockwise to the next empty position, and causing the lower cartridge 234 to rotate counter-clockwise to the next position containing a clean probe. As the lower cartridge 234 rotates, the adjacent probe tube with a clean probe advances to align with the hole in the output port 209, and the clean probe 5 drops into the tonometer 1.

Figure 19:
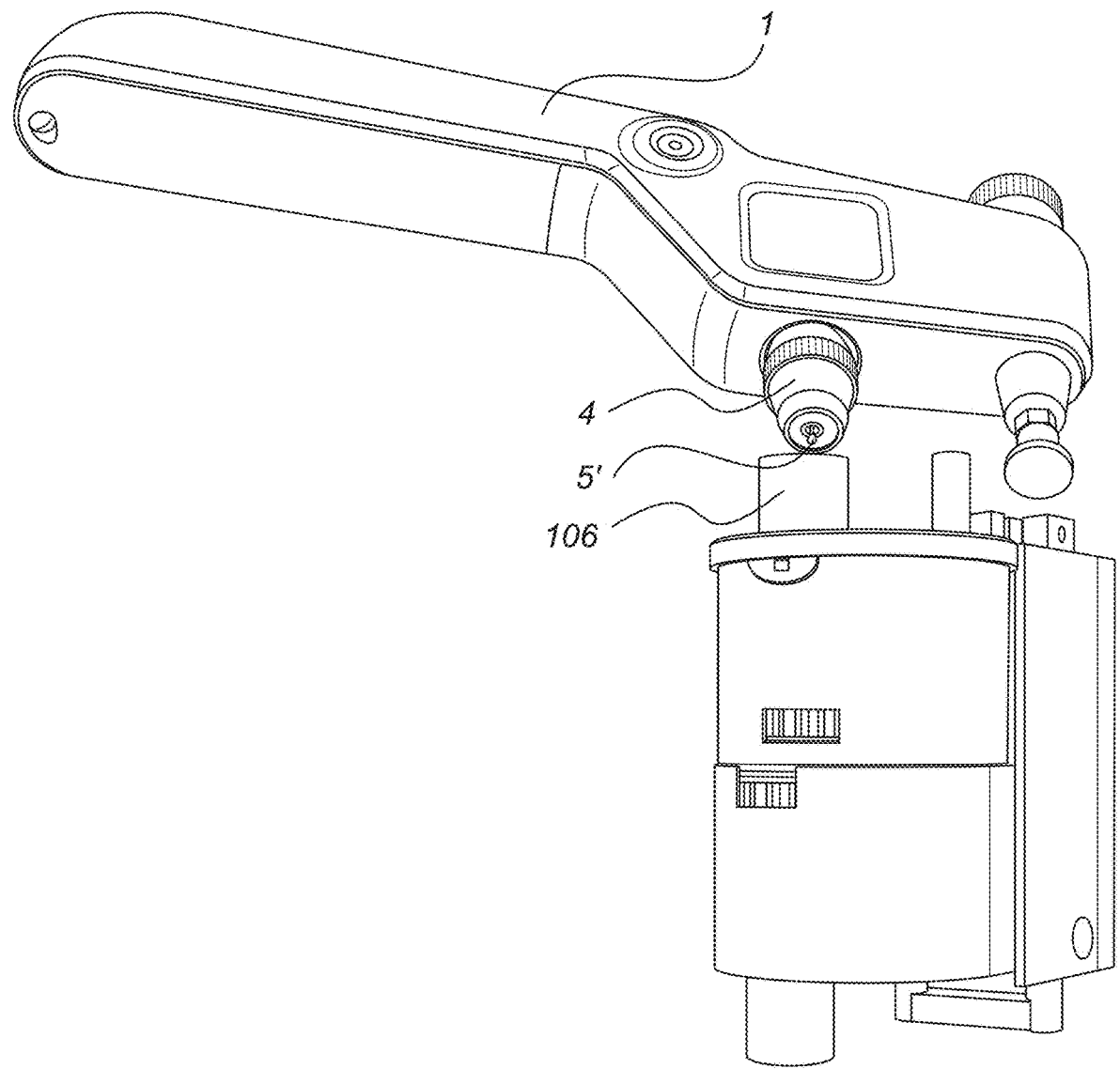
FIG. 19 shows how to discharge a contaminated probe from the tonometer.

FIG. 19 shows how to discharge the contaminated probe from the tonometer. The tonometer 1 is held above the input port 206 of the present invention such that the cone 4 of the tonometer is able to drop the contaminated probe 5' into the input port 206 into the empty tube of the upper cartridge, which had already been advanced when the upper activator rod 205 was pressed previously to dispense a clean probe 5 from the lower cartridge. Once the power of the tonometer is off, the probe falls through the hole in the input port 206 of the lid, and then into the empty probe tube which is aligned with the hole. The upper cartridge will advance to the next empty probe tube when the next clean probe is dispensed, thus eliminating the need to press the actuator rod twice.

Figure 20A:
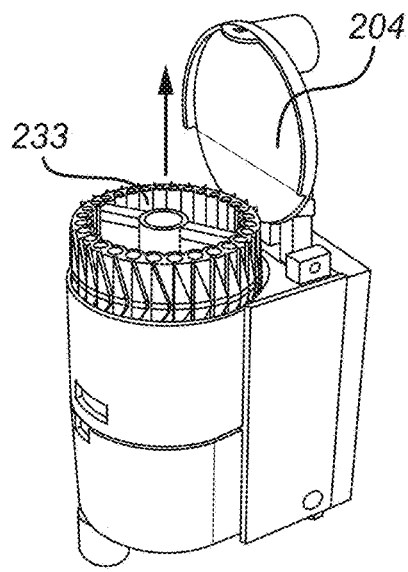
FIGS. 20A-20D show the disinfection cycling of cartridges.
Figure 20B:
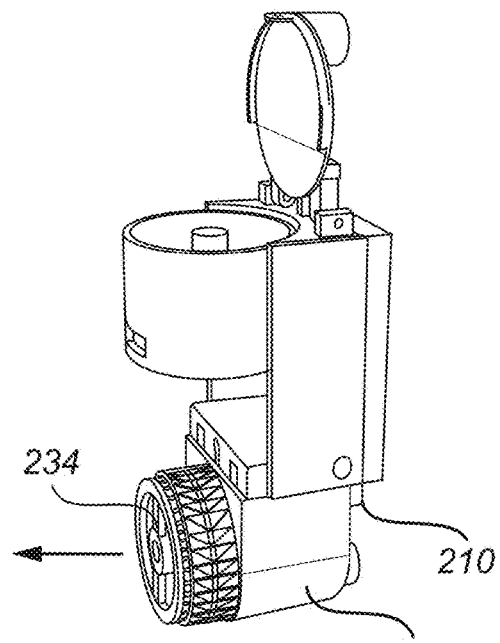
Figure 20C:
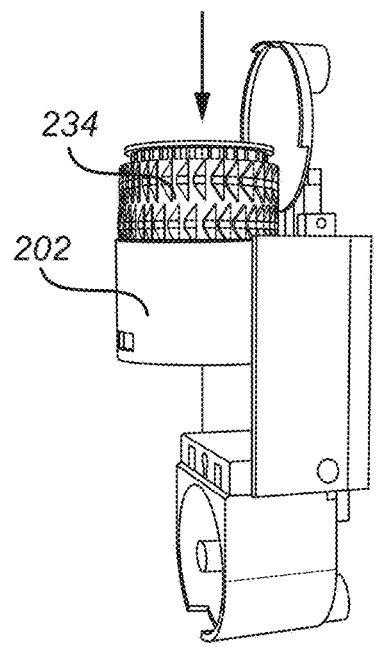
Figure 20D:
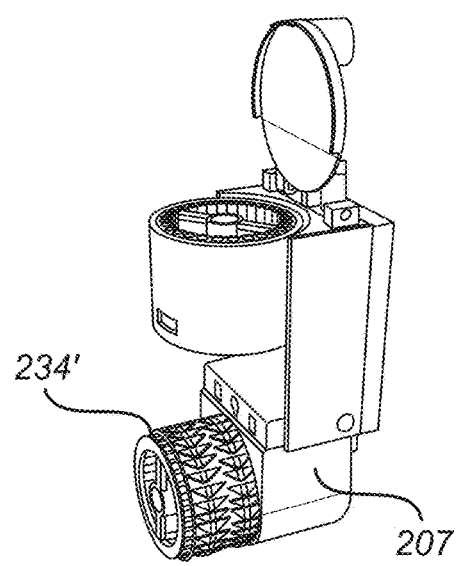

FIGS. 20A-20D show the disinfection cycling of the cartridges. In FIG. 20A, the lid 204 is opened, and the upper cartridge 233 which is full of contaminated probes is removed and soaked in a disinfecting solution. In FIG. 20B, the releasing bracket 210 is pressed to open the rotating lower compartment 207, containing the lower cartridge 234, which is now empty. In FIG. 20C, the empty lower cartridge 234 is then rotated and inserted into the upper compartment 202 and is now ready to receive the contaminated probes. In FIG. 20D, a cartridge which has been disinfected 234' is then inserted into the rotating lower compartment 207 so that it will be in an inverted position once the lower compartment is closed. Some embodiments include an indicator that displays how many times the lower (or upper) compartment has been opened. In this manner, the user can track how many times probes have been cycled through the System.

Figure 21A:
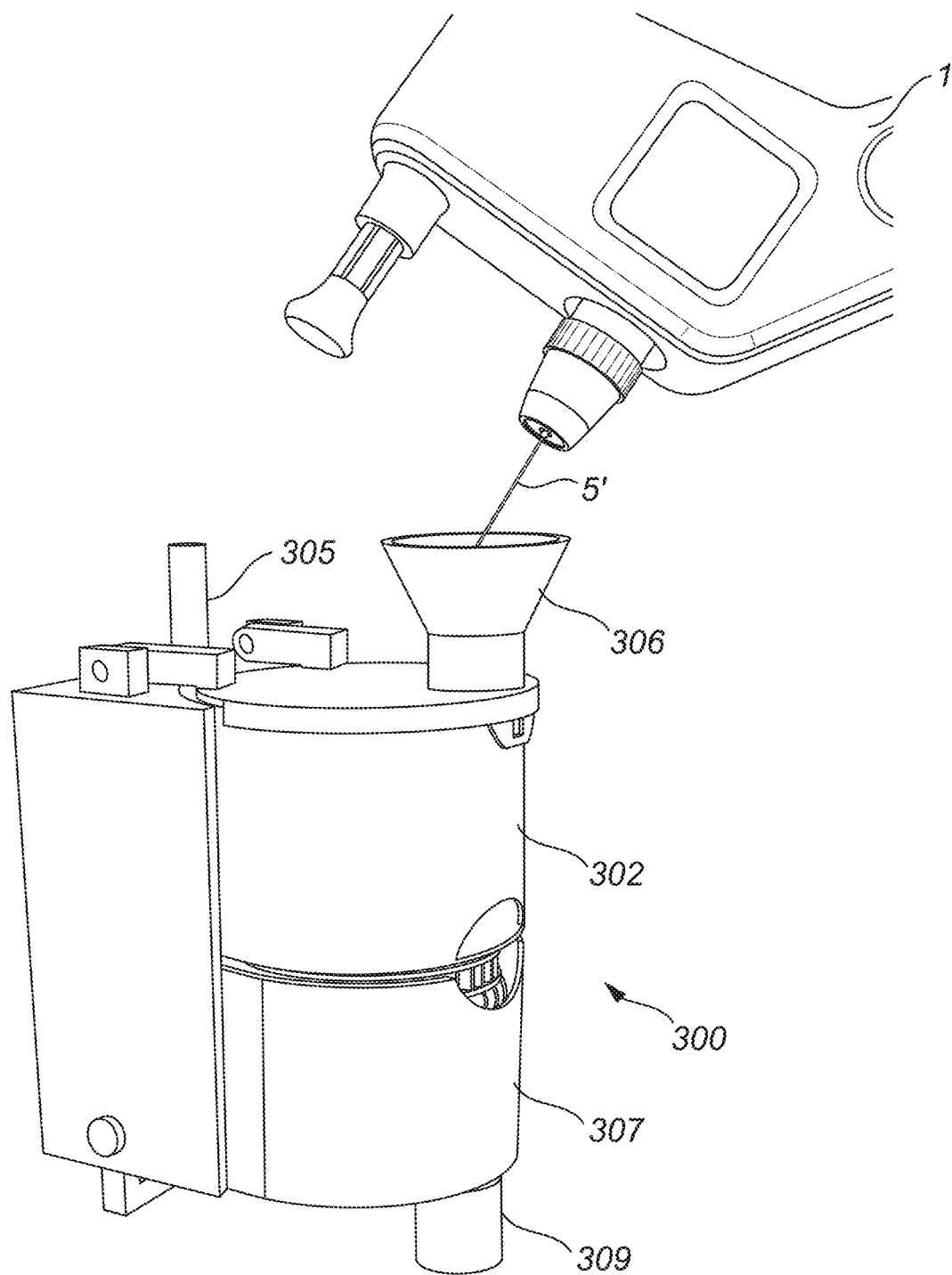
FIGS. 21A and 21B illustrate the configuration and operation of a third embodiment.
Figure 21B:
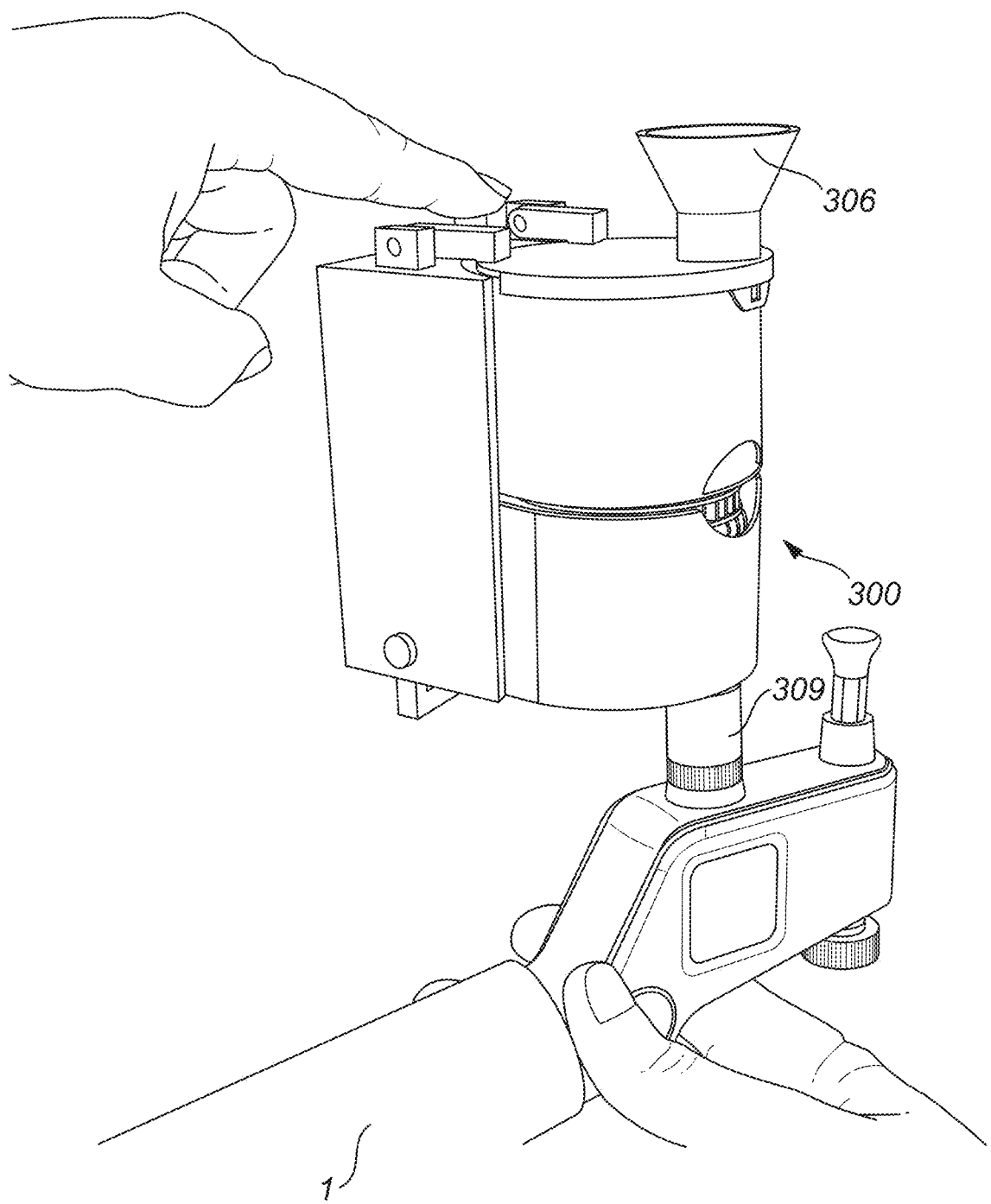

FIGS. 21A and 21B illustrate the configuration and operation of a third embodiment. In FIG. 21A, the System 300 includes an upper compartment 302, an actuator 305, a lower compartment 307, a funnel-shaped input port 306, and a cup-shaped output port 309. The illustrated embodiment of the System 300 is similar to the second embodiment, except that it has a funnel-shaped input port 306 instead of a cup-shaped input port. FIG. 21A shows the discharge of a used probe. The user (not shown) holds and tilts the tonometer 1 such that the used tonometer probe 5' drops out of the tonometer 1 and into the cartridge held within the upper compartment 302 via the funnel-shaped input port 306.

FIG. 21B shows the insertion of a clean probe into the tonometer 1. The user first mates the tonometer 1 with the output port 309. The user then depresses the actuator rod 305. As discussed above, depressing the actuator rod rotates the lower cartridge housed in the lower compartment 307 such that a tube holding a clean probe aligns with the output port 309, causing the clean probe to fall through the output port and into the tonometer 1. At the same time, depressing the actuator rod 305 also causes the upper cartridge housed in the upper compartment 302 to rotate such that an empty tube aligns with the input port 306, making the System 300 ready to receive another used probe.

Figure 22:
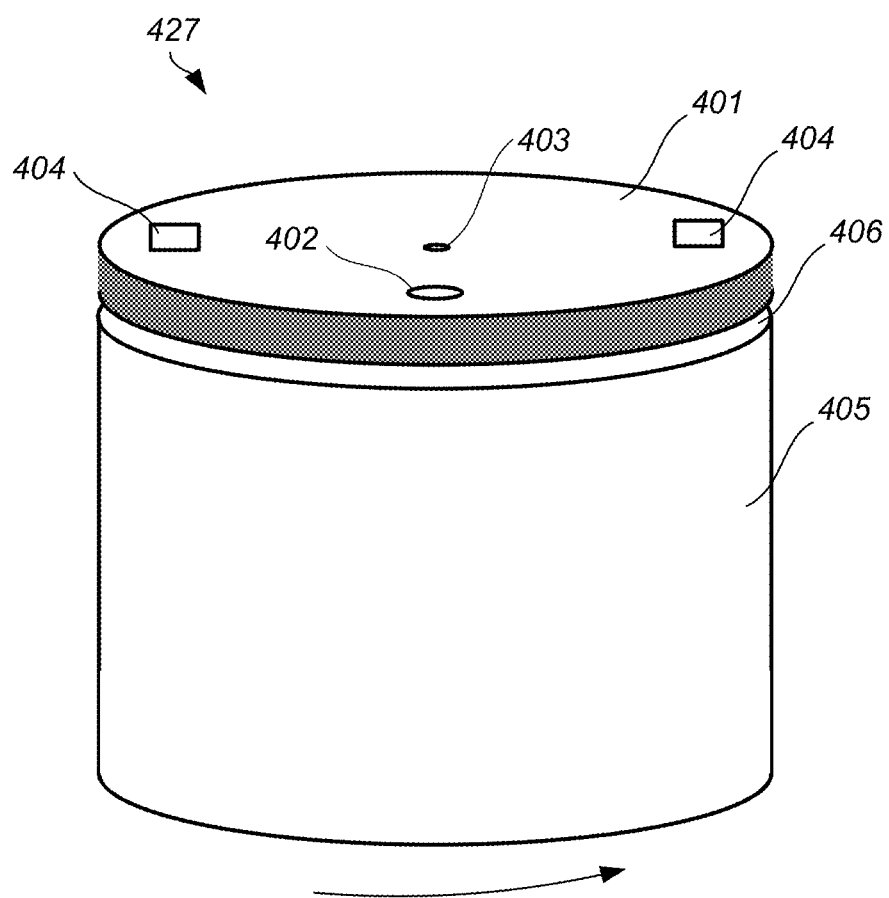
FIG. 22 shows a probe cartridge according to a fourth embodiment.

FIG. 22 shows a probe cartridge 427 according to a fourth embodiment. The probe cartridge includes a lid 401, which has a hole 402, an axis 403, and one or more raised tabs 404. The probe cartridge also includes a base 405 which houses a plurality of tonometer tubes as described above. The lid 401 is separated by a gap 406 from the base 405. The gap (and possibly other openings in the base 405) allow fluid passage into and out of the tubes held within the base 405. The lid 401 is also rotatable with respect to the base 405 and vice versa.

In this embodiment, a cartridge holding clean probes can be tipped "upside down" (with the lid 401 at bottom) without any of the probes falling out, with the possible exception of a probe contained within a tube that is aligned with the hole 402. When the cartridge 427 is flipped upside down, the lid 401 becomes a "floor" for the cartridge. The lid 401 can be held in place via the tabs 404, such that the base can rotate with respect to the lid in order to align internal tubes with the hole 402.

The ability to hold a full cartridge 427 in an upside-down position simplifies the mechanical structure of the housing by eliminating the need for a hinged compartment that rotates from a vertical to horizontal (loading) orientation. Instead, the lower compartment may have a hinged lid similar to the upper compartment, except that the compartment lid is located at the bottom of the lower compartment. To load, a full cartridge 427 is flipped over (so its rotating lid is at bottom and the probes are pointing upward) and the cartridge is pushed upward into the lower compartment. The compartment lid is then closed and latched so that the cartridge is held within the compartment. The tabs 404 engage with a receiver in the compartment lid so that the cartridge lid 401 and hole 402 is held in place in alignment with the output port of the lower compartment as the 405 rotates to dispense clean probes.

In a variation that also uses the cartridge 427 (or similar with a rotating lid), the lower compartment has a "door" with a vertical hinge that opens by swinging in the horizontal plane. This door provides access to the inside of the lower compartment and allows a full cartridge 427 (upside down, with rotating lid at bottom and probes pointing upward) to be slid (along the horizontal plane) into the compartment. The tabs 404 may engage into a groove, channel, or similar receiver in the base of the lower compartment in order to force the cartridge into an orientation that aligns the cartridge hole 402 with the hole and output port of the lower compartment.

In some embodiments, the System may also include other components, such as a disinfection bath. The bath contains disinfecting fluid and is sized to hold one or more cartridges of tonometer tubes. When a given cartridge is full of used tubes, the user places the cartridge in the bath. Some embodiments of the bath may include a timer and an indicator to remind the user when the cartridge has been in the bath for a sufficiently long period of time. The indicator may be visual (e.g., a blinking light), audio (e.g., a bell), or the like. In some embodiments the bath may transmit a message to the user, such as via an app or SMS messaging to a mobile phone. Some embodiments include an indicator associated with the bath that displays how many times the bath has been used. The indicator could count up, count down, or give a notification when a predetermined number of cycles have been completed. In this manner, the user can track how many times probes have been cycled through the System.

Further variations to embodiments described herein are contemplated. For example, while above embodiments rely on an actuator rod to cause rotation of one or more cartridges, other embodiments may include a button that causes an electrical signal to activate a motor (e.g., a stepper motor) coupled to gearing or a belt that rotates the one or more cartridges. Instead of a button, a hands-free mechanism may also or instead be used to reduce or eliminate the need to touch the System when cycling tonometer probes. For example, the System may include a microphone and voice activation hardware/software, so that the user can command the System to dispense a new probe or perform other functions. As another alternative, the System may include a proximity sensor, RFID reader, or other input device configured to detect a controlling input from a user.

Although several embodiments herein are based upon two cylindrical cartridges aligned on their central axes and arranged one atop the other, other embodiments may use a side-by-side arrangement for two cartridges. For example, in an embodiment that uses a cartridge with rotating lid as shown in FIG. 22, the housing may have one or more front-facing doors that allow insertion of cartridges in the horizonal plane.

While the described embodiments are primarily based on cylindrical arrangement of tonometer tubes, other arrangements can be employed. For example, other embodiments may use a linear array of tubes that are shifted from one end to another into alignment with an input or output port to receive or dispense tonometer probes.

Figure 23:
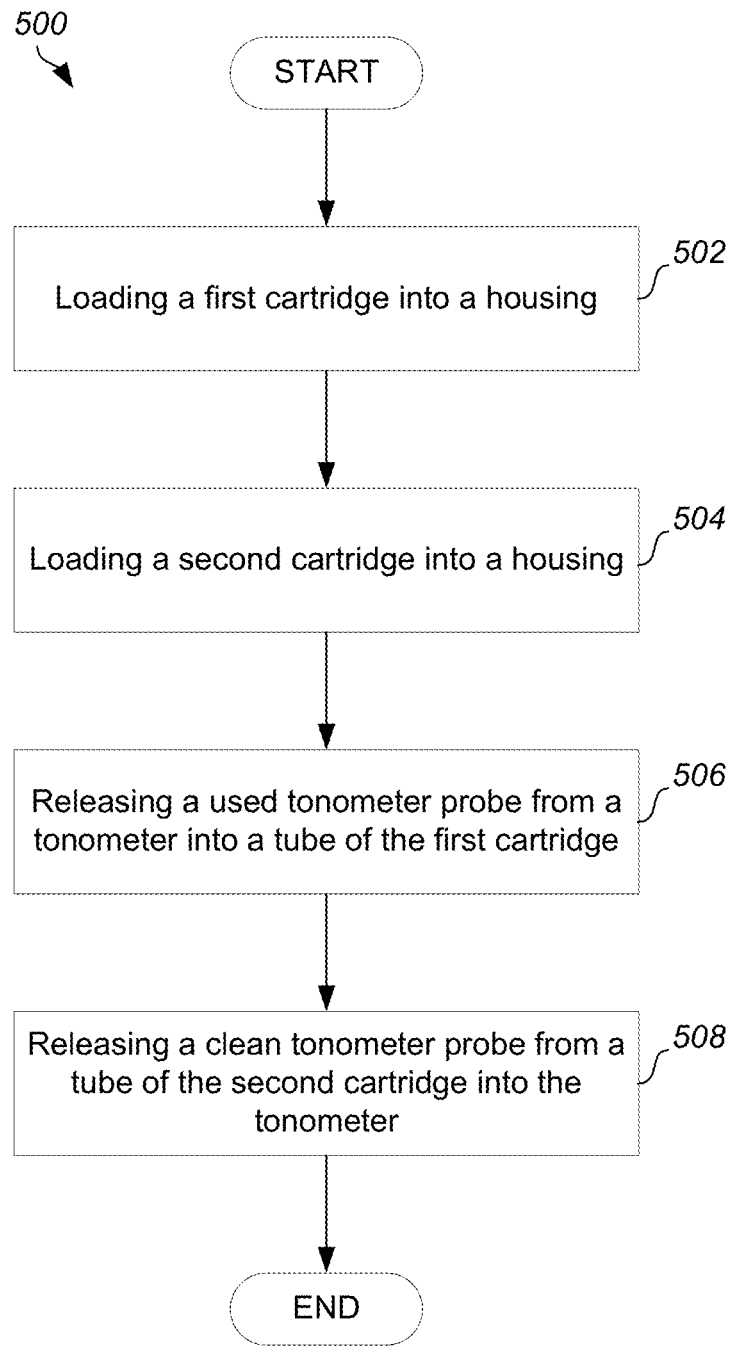
FIG. 23 is a flow diagram of a process according to some embodiments.

FIG. 23 is a flow diagram of a process 500 according to one embodiment. The process 500 begins at block 502, where a user loads a first cartridge into a housing. The first cartridge includes a plurality of tubes that are configured to hold contaminated tonometer probes. The tubes may be arranged and structured as described above with respect to various embodiments.

At block 504, the user loads a second cartridge into the housing. The second cartridge includes a plurality of tubes that are configured to hold disinfected tonometer probes.

The second cartridge is initially full of clean probes and is typically loaded upside down with respect to the first cartridge.

At block 506, the user releases a used tonometer probe from a tonometer into one of the plurality of tubes of the first cartridge. The tube passes through an input port of the housing, such as a cup-shaped, funnel-shaped, or similar passage component of the housing.

At block 508, the user releases into the tonometer a clean tonometer probe from a tube of the second cartridge. In some embodiments, the tonometer is first mated with the housing via an outport port of the housing.

Other operations may be performed instead of or in addition to those above. For example, as part of block 508, the user may advance the first and second cartridges, such as by rotating the cartridges as described above. Advancing the cartridge exposes an empty one of the plurality of tubes of the first cartridge to make a space to receive the next used probe. Advancing the cartridge also releases the disinfected tonometer probe from the second cartridge into the tonometer. Furthermore, at some later time when the first cartridge is full of used probes, the user may remove the first cartridge and place it into a disinfection bath. At this time, the user then reloads the System by inserting an empty first cartridge for used probes and a second cartridge that is full of clean probes. Note that once the disinfection period has passed, the first cartridge will contain clean probes and can be inserted into the housing as the "clean cartridge."

Note also that the steps of process 500 may be performed in different orders. For example, in some embodiments a clean probe is first received from the housing. Then the probe is used and thereafter the used probe is released back to the housing.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A system for managing a plurality of tonometer probes, comprising:
   a housing configured to support first and second compartments, the housing comprising:
   a first compartment for holding contaminated tonometer probes, wherein
   the first compartment has an input port and is configured to hold a first cylindrical cartridge that has a central axis and that holds a first plurality of tubes circularly arranged about the central axis of the cartridge, each tube having an open end that points upward to receive tonometer probes, and
   the first cartridge is configured to rotate about the central axis such that each of the tubes can be aligned with the input port to receive a contaminated probe from the tonometer; and
   a second compartment for holding disinfected tonometer probes, wherein
   the second compartment has an output port and is configured to hold a second cylindrical cartridge that has a central axis and that holds a second plurality of tubes circularly arranged about the central axis of the cartridge, each tube having an open end that points downward to dispense clean disinfected tonometer probes, and
   the second cartridge is configured to rotate about the central axis such that each of the tubes can be aligned with the output port to dispense a disinfected probe to the tonometer.

2. The system of claim 1, wherein the first and second cartridges are removable from the housing.

3. The system of claim 1, wherein the first compartment is an upper compartment, wherein the second compartment is a lower compartment, wherein the upper compartment is above the lower compartment, and wherein the upper and lower compartments are each openable to receive a cartridge.

4. The system of claim 3, wherein the housing further comprises:
   a lid that provides access to the upper compartment, such that the upper compartment can receive the first cartridge when the lid is opened, wherein alignment of the first cartridge includes any angle at which the probe will fall into the tube by force of gravity; and
   a hinge connected to the lower compartment that allows the lower compartment to be rotated between closed and open positions, wherein an alignment of the second cartridge in the closed position includes any angle at which the probe will fall out of the tube by force of gravity and the alignment of the second cartridge in the open position includes any angle that will keep the probe from falling out of the tube.

5. The system of claim 1, further comprising an indicator that displays how many times the first or second compartment has been opened.

6. The system of claim 1, wherein the first and/or second compartment is moveable to facilitate loading of a cartridge.

7. The system of claim 1, wherein the first and second cartridges are held by the housing such that a central axis of the first cartridge is in alignment with a central axis of the second cartridge.

8. The system of claim 1, wherein the output port is a cup-like structure configured to mate with the tonometer to facilitate passage of a disinfected tonometer probe from the second cartridge into the tonometer.

9. The system of claim 1, further comprising an indicator that signals that the first cartridge is full or that the second cartridge is empty.

10. The system of claim 1, wherein the first cylindrical cartridge includes:
    a base that contains the first plurality of tubes of the first cartridge; and
    a lid that is configured to rotate with respect to the base, wherein the lid includes a hole that is alignable with each of the first plurality of tubes of the first cartridge.

11. The system of claim 1, further comprising an indicator that displays how many disinfected probes remain in the system.

12. The system of claim 1, further comprising an indicator that displays how many contaminated probes remain in the system.

13. The system of claim 1, further comprising a disinfection bath configured to hold the first and/or second plurality of tubes.

14. The system of claim 13, wherein the bath includes an indicator to notify a user that a period of time has passed and/or to notify the user based on a number of times that bath has been used.

15. A method for managing a plurality of tonometer probes, comprising:
    using the system of claim 1, by:
    loading the first cartridge into the first compartment;

loading the second cartridge into the second compartment;

releasing, via the access port of the housing, the contaminated tonometer probe into one of the plurality of tubes of the first cartridge;

mating the tonometer with the housing via the output port;

releasing the disinfected tonometer probe from one of the plurality of tubes of the second cartridge; and receiving the disinfected tonometer probe into the tonometer.

16. The method of claim 15, further comprising advancing the first and second cartridges, thereby exposing an empty one of the plurality of tubes of the first cartridge.

17. The method of claim 15, further comprising:

removing the first cartridge from the first compartment; and placing the first cartridge in a disinfection bath.

18. The method of claim 17, further comprising:

after a disinfection period has passed, removing the first cartridge from the disinfection bath; and loading the first cartridge into the second compartment, the first cartridge now holding disinfected tonometer probes.

19. A system for managing a plurality of tonometer probes, comprising:

a first compartment for holding contaminated tonometer probes, wherein the first compartment has an input port and is configured to hold a first cylindrical cartridge that has a central axis and that holds a first plurality of tubes circularly arranged about the central axis of the cartridge, and the first cartridge is configured to rotate about the central axis such that each of the tubes can be aligned with the input port to receive a contaminated probe from the tonometer; and a second compartment for holding disinfected tonometer probes, wherein the second compartment has an output port and is configured to hold a second cylindrical cartridge that has a central axis and that holds a second plurality of tubes circularly arranged about the central axis of the cartridge, and the second cartridge is configured to rotate about the central axis such that each of the tubes can be aligned with the output port to dispense a disinfected probe to the tonometer; and an actuator that causes the first and second cartridges to rotate in unison, such that the first cartridge advances to align an empty tube with the input port and the second cartridge advances to dispense the disinfected tonometer probe into the tonometer via the output port.

20. The system of claim 19, wherein the actuator is a rod, and wherein the rod includes a first tab that engages an outer surface of the first cartridge when the rod moves in a downward position thereby advancing the first cartridge rotationally about the central axis of the first cartridge.

21. The system of claim 20, wherein the rod includes a second tab that engages an outer surface of the second cartridge when the rod moves in an upward position, thereby advancing the second cartridge rotationally about the central axis of the second cartridge, wherein the rod is biased upwards by a spring.

22. The system of claim 19, wherein the actuator is a stepper motor.

23. The system of claim 19, wherein the actuator is a lever that, when engaged by a user, causes rotation of each of the first and second cartridges in unison.

24. A system for managing a plurality of tonometer probes, comprising:

a first compartment for holding contaminated tonometer probes, wherein the first compartment has an input port and is configured to hold a first cylindrical cartridge that has a central axis and that holds a first plurality of tubes circularly arranged about the central axis of the cartridge, and the first cartridge is configured to rotate about the central axis such that each of the tubes can be aligned with the input port to receive a contaminated probe from the tonometer; and a second compartment for holding disinfected tonometer probes, wherein the second compartment has an output port and is configured to hold a second cylindrical cartridge that has a central axis and that holds a second plurality of tubes circularly arranged about the central axis of the cartridge, and the second cartridge is configured to rotate about the central axis such that each of the tubes can be aligned with the output port to dispense a disinfected probe to the tonometer, wherein each of the tubes has an open proximal end and a closed distal end, and each of the tubes includes at least one of:

an opening in a sidewall near the distal end, or an opening in the distal end having a circumference smaller than a circumference of the probe.

\* \* \* \* \*